US012655445B2

(12) United States Patent
Kadlec et al.

(10) Patent No.: US 12,655,445 B2
(45) Date of Patent: Jun. 16, 2026

(54) INTRALUMINAL STENTS FOR TREATING BENIGN PROSTATIC HYPERPLASIA

(71) Applicant: Rivermark Medical, Inc., Milwaukee, WI (US)

(72) Inventors: Adam Kadlec, Milwaukee, WI (US); Andrew Schieber, Tustin, CA (US); Anand Doraiswamy, Oakland, CA (US)

(73) Assignee: Rivermark Medical, Inc., Milwaukee, WI (US)

( * ) Notice: Subject to any disclaimer, the term of this patent is extended or adjusted under 35 U.S.C. 154(b) by 0 days.

(21) Appl. No.: 18/433,302

(22) Filed: Feb. 5, 2024

(65) Prior Publication Data

US 2024/0225813 A1     Jul. 11, 2024

Related U.S. Application Data

(63) Continuation-in-part of application No. PCT/US2022/039481, filed on Aug. 4, 2022.

(Continued)

(51) Int. Cl.
A61F 2/04          (2013.01)
A61B 1/018         (2006.01)
(Continued)

(52) U.S. Cl.
CPC .............. C12N 15/85 (2013.01); A61B 1/018 (2013.01); A61B 1/307 (2013.01); A61F 2/04 (2013.01);
(Continued)

(58) Field of Classification Search
CPC .................... A61F 2002/047; A61F 2002/048
(Continued)

(56) References Cited

U.S. PATENT DOCUMENTS 4,893,623 A * 1/1990 Rosenbluth ............. A61F 2/915
                                                     604/104
5,059,169 A    10/1991 Zilber
                (Continued)

FOREIGN PATENT DOCUMENTS

CN        106901880        6/2017
DE         3417738        11/1985
                (Continued)

OTHER PUBLICATIONS

International Preliminary Report on Patentability for PCT/US2022/039481, issued Feb. 6, 2024 in 9 pages.
(Continued)

*Primary Examiner* — Katrina M Stransky
(74) *Attorney, Agent, or Firm* — Knobbe, Martens, Olson & Bear, LLP

(57)                    ABSTRACT

A device for maintaining patency of a prostatic urethra includes a stent having a proximal end, a distal end, and a passageway therebetween. The device includes longitudinal and angled struts and nodes, each longitudinal strut coupled to at least one angled strut at a corresponding node, the struts and nodes coupled to each other to form a plurality of cells, circumferentially adjacent cells forming stent regions. The stent includes a nose region, a body region, and a tail region. The stent is configured to expand from a compressed configuration to an expanded configuration within a bodily lumen. The stent includes a collapsibility gradient along its length such that it provides a nose region radial force at the nose region, a body region radial force at the body region, and a tail region radial force at the tail region, wherein the nose region radial force is less than the tail region radial force, and the tail region radial force is less than the body region radial force.

23 Claims, 22 Drawing Sheets

Related U.S. Application Data

(60) Provisional application No. 63/230,602, filed on Aug. 6, 2021.

(51) Int. Cl.

| | |
|---|---|
| *A61B 1/307* | (2006.01) |
| *C07K 14/005* | (2006.01) |
| *C12N 9/22* | (2006.01) |
| *C12N 15/11* | (2006.01) |
| *C12N 15/85* | (2006.01) |
| *C12N 15/90* | (2006.01) |
| *A61F 2/966* | (2013.01) |

(52) U.S. Cl.
CPC .............. *C07K 14/005* (2013.01); *C12N 9/22* (2013.01); *C12N 15/11* (2013.01); *C12N 15/907* (2013.01); *A61F 2002/047* (2013.01); *A61F 2002/9665* (2013.01); *A61F 2210/0014* (2013.01); *A61F 2210/0076* (2013.01); *A61F 2220/0008* (2013.01); *A61F 2230/0026* (2013.01); *A61F 2250/001* (2013.01); *A61F 2250/0039* (2013.01); *C12N 2310/20* (2017.05); *C12N 2310/531* (2013.01); *C12N 2330/50* (2013.01); *C12N 2800/107* (2013.01); *C12N 2800/80* (2013.01)

(58) Field of Classification Search
USPC ...................................................... 623/23.66
See application file for complete search history.

(56) References Cited

U.S. PATENT DOCUMENTS

| | | | |
|---|---|---|---|
| 5,064,435 | A | 11/1991 | Porter |
| 5,246,445 | A | 9/1993 | Yachia et al. |
| 5,466,242 | A | 11/1995 | Mori |
| 5,496,365 | A | 3/1996 | Sgro |
| 5,667,486 | A | 9/1997 | Mikulich et al. |
| 5,735,871 | A | 4/1998 | Sgro |
| 6,019,779 | A | 2/2000 | Thorud et al. |
| 6,022,312 | A | 2/2000 | Chaussy et al. |
| 6,139,536 | A | 10/2000 | Mikus et al. |
| 6,183,507 | B1 | 2/2001 | Lashinski et al. |
| 6,305,436 | B1 | 10/2001 | Andersen et al. |
| 6,315,791 | B1 | 11/2001 | Gingras et al. |
| 6,436,133 | B1 | 8/2002 | Furst et al. |
| 6,494,908 | B1 | 12/2002 | Huxel et al. |
| 6,702,846 | B2 | 3/2004 | Mikus et al. |
| 6,733,536 | B1 | 5/2004 | Gellman |
| 6,852,124 | B2 | 2/2005 | Cox et al. |
| 6,911,041 | B1 | 6/2005 | Zscheeg |
| 7,112,226 | B2 | 9/2006 | Gellman |
| 7,169,187 | B2 | 1/2007 | Datta et al. |
| 7,485,130 | B2 | 2/2009 | St. Germain |
| 7,527,651 | B2 | 5/2009 | Gellman |
| 7,780,719 | B2 | 8/2010 | Killion et al. |
| 7,935,142 | B2 | 5/2011 | Gregorich |
| 7,993,387 | B2 | 8/2011 | Clerc et al. |
| 8,287,602 | B2 | 10/2012 | Daignault et al. |
| 8,357,179 | B2 | 1/2013 | Grandfield et al. |
| 8,465,551 | B1 | 6/2013 | Wijay et al. |
| 8,506,619 | B2 | 8/2013 | Ortiz et al. |
| 8,512,392 | B2 | 8/2013 | Bidne et al. |
| 8,529,596 | B2 | 9/2013 | Grandfield et al. |
| 8,591,569 | B2 | 11/2013 | Shin et al. |
| 8,603,187 | B2 | 12/2013 | Kilemnick et al. |
| 8,709,060 | B2 | 4/2014 | Osborne |
| 8,795,345 | B2 | 8/2014 | Grandfield et al. |
| 9,044,263 | B2 | 6/2015 | Grandfield et al. |
| 9,072,537 | B2 | 7/2015 | Grandfield et al. |
| 9,138,336 | B2 | 9/2015 | Carman et al. |
| 9,307,996 | B2 | 4/2016 | Johnson et al. |
| 9,549,739 | B2 | 1/2017 | Catanese, III et al. |
| 9,603,733 | B2 | 3/2017 | Shobavashi |
| 9,848,905 | B2 | 12/2017 | Kilemnik |
| 10,035,005 | B2 | 7/2018 | Bar-On et al. |
| 10,105,132 | B2 | 10/2018 | Lamson et al. |
| 10,195,014 | B2 | 2/2019 | Lamson et al. |
| 10,271,977 | B2 | 4/2019 | Longo et al. |
| 10,406,333 | B2 | 9/2019 | Feld |
| 10,441,447 | B2 | 10/2019 | Krieger et al. |
| 10,478,283 | B2 | 11/2019 | Bachar |
| 10,492,792 | B2 | 12/2019 | Catanese, III et al. |
| 10,507,122 | B2 | 12/2019 | Bachar |
| 10,555,802 | B1 | 2/2020 | Shadduck |
| 10,660,772 | B2 | 5/2020 | Schwartz et al. |
| 10,682,245 | B2 | 6/2020 | Harkin et al. |
| 10,828,184 | B1 | 11/2020 | Schwartz |
| 10,881,539 | B2 | 1/2021 | Harkin et al. |
| 10,912,637 | B2 | 2/2021 | Lamson et al. |
| 10,932,927 | B2 | 3/2021 | Clinger et al. |
| 10,952,885 | B2 | 3/2021 | Sicotte et al. |
| 10,966,813 | B2 | 4/2021 | Shadduck |
| 11,027,106 | B2 | 6/2021 | Bachar |
| 11,096,774 | B2 | 8/2021 | Sicotte et al. |
| 11,273,025 | B2 | 3/2022 | Ghriallais et al. |
| 11,285,027 | B1 | 3/2022 | Chanduszko et al. |
| 11,304,724 | B2 | 4/2022 | Kilemnik |
| 11,471,148 | B2 | 10/2022 | Lamson et al. |
| 11,484,398 | B2 | 11/2022 | Ghriallais et al. |
| 11,497,637 | B2 | 11/2022 | Huang et al. |
| 11,571,290 | B2 | 2/2023 | Bachar |
| 11,602,621 | B2 | 3/2023 | Ghriallais et al. |
| 2002/0099438 | A1 | 7/2002 | Furst |
| 2002/0161427 | A1 | 10/2002 | Rabkin et al. |
| 2003/0040803 | A1 | 2/2003 | Rioux et al. |
| 2003/0045923 | A1* | 3/2003 | Bashiri ................. A61F 2/915 623/1.12 |
| 2004/0102833 | A1 | 5/2004 | Girton et al. |
| 2004/0249343 | A1* | 12/2004 | Cioanta ................. A61B 18/04 604/113 |
| 2006/0004436 | A1 | 1/2006 | Amarant et al. |
| 2006/0142849 | A1 | 6/2006 | Killion et al. |
| 2006/0276871 | A1 | 12/2006 | Lamson et al. |
| 2007/0173921 | A1 | 7/2007 | Wholey et al. |
| 2008/0132998 | A1* | 6/2008 | Mangiardi ............... A61F 2/91 623/1.17 |
| 2009/0105719 | A1 | 4/2009 | Honey et al. |
| 2009/0149935 | A1 | 6/2009 | Chu et al. |
| 2009/0210045 | A1 | 8/2009 | Sorensen et al. |
| 2010/0130815 | A1 | 5/2010 | Gross et al. |
| 2011/0098825 | A1 | 4/2011 | Shin et al. |
| 2011/0276038 | A1 | 11/2011 | McIntyre et al. |
| 2012/0158155 | A1 | 6/2012 | Shin |
| 2012/0271405 | A1 | 10/2012 | Soletti et al. |
| 2013/0144372 | A1 | 6/2013 | Wood et al. |
| 2013/0325141 | A1 | 12/2013 | Gill et al. |
| 2014/0025151 | A1* | 1/2014 | Gao .......................... A61F 2/86 623/1.13 |
| 2016/0242894 | A1 | 8/2016 | Davis |
| 2017/0027724 | A1 | 2/2017 | Hossainy et al. |
| 2017/0216062 | A1 | 8/2017 | Armstrong et al. |
| 2017/0333230 | A1 | 11/2017 | Folan et al. |
| 2018/0021155 | A1 | 1/2018 | Hadley et al. |
| 2018/0264226 | A1 | 9/2018 | Erbey, II et al. |
| 2018/0318114 | A1 | 11/2018 | Huang et al. |
| 2019/0117423 | A1 | 4/2019 | Chao et al. |
| 2019/0224008 | A1 | 7/2019 | Bressloff et al. |
| 2020/0038213 | A1 | 2/2020 | Bly et al. |
| 2020/0323618 | A1 | 10/2020 | Bly et al. |
| 2020/0368008 | A1 | 11/2020 | Koroschetz |
| 2021/0022594 | A1 | 1/2021 | Jen et al. |
| 2021/0022893 | A1 | 1/2021 | Itoi et al. |
| 2021/0059704 | A1 | 3/2021 | Kilemnik |
| 2021/0145617 | A1 | 5/2021 | Doi |
| 2021/0145619 | A1 | 5/2021 | Bly et al. |
| 2021/0161642 | A1 | 6/2021 | Jen et al. |
| 2021/0307942 | A1 | 10/2021 | Flora et al. |
| 2022/0015889 | A1* | 1/2022 | Lima ................. A61B 1/00154 |
| 2022/0079736 | A1 | 3/2022 | Sicotte et al. |
| 2022/0104845 | A1 | 4/2022 | Golan et al. |
| 2022/0110737 | A1 | 4/2022 | Mehta et al. |

(56) References Cited

U.S. PATENT DOCUMENTS

| | | | |
|---|---|---|---|
| 2022/0167921 | A1 | 6/2022 | Aljuri et al. |
| 2022/0313457 | A1 | 10/2022 | Brown et al. |
| 2022/0395363 | A1 | 12/2022 | Ghriallais et al. |
| 2023/0092775 | A1 | 3/2023 | Juan et al. |
| 2023/0200972 | A1 | 6/2023 | Bachar |
| 2024/0115405 | A1 | 4/2024 | Kadlec |

FOREIGN PATENT DOCUMENTS

| | | |
|---|---|---|
| DE | 19653719 | 4/1998 |
| EP | 0566807 | 10/1993 |
| KR | 2013-0126776 A | 11/2013 |
| WO | WO 1997/12562 | 4/1997 |
| WO | WO 2005/110285 | 11/2005 |
| WO | WO 2007/070788 | 6/2007 |
| WO | WO 2009/099632 | 8/2009 |
| WO | WO 2011/034768 | 3/2011 |
| WO | WO 2019/237071 | 12/2019 |
| WO | WO 2022/058751 | 3/2022 |
| WO | WO 2023/014917 | 2/2023 |
| WO | WO 2024/064905 | 3/2024 |

OTHER PUBLICATIONS

International Search Report and Written Opinion for PCT/US2019/036162, mailed Sep. 18, 2019 in 19 pages.

International Preliminary Report on Patentability and Written Opinion for PCT/US2019/036162, issued Dec. 8, 2020 in 14 pages.

International Search Report and Written Opinion for PCT/US2022/039481, mailed Nov. 16, 2022 in 18 pages.

International Search Report and Written Opinion for PCT/US2023/074925, mailed Jan. 19, 2024 in 9 pages.

\* cited by examiner

Catheter Tube 702

Port 716

Handpiece 704

Flexible delivery scope; cystoscope as delivery instrument 700

Eyepiece 706

Working channel/irrigation 710

Illumination 712

Camera 714

Cystoscope distal end 718

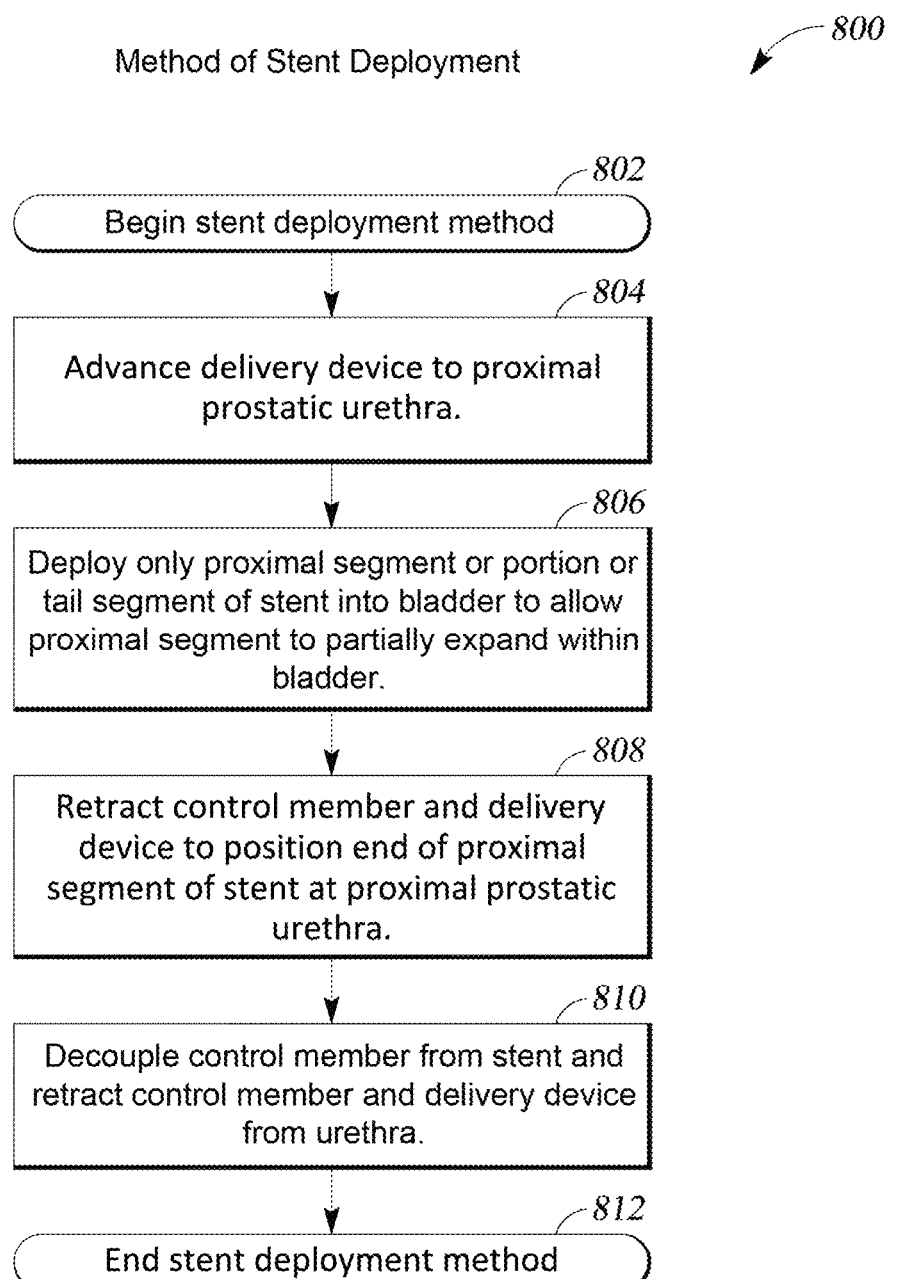

Method of Stent Deployment

*800*

*802*

Begin stent deployment method

*804*

Advance delivery device to proximal prostatic urethra.

*806*

Deploy only proximal segment or portion or tail segment of stent into bladder to allow proximal segment to partially expand within bladder.

*808*

Retract control member and delivery device to position end of proximal segment of stent at proximal prostatic urethra.

*810*

Decouple control member from stent and retract control member and delivery device from urethra.

*812*

End stent deployment method

*FIG. 8*

Method of Stent Retrieval

Method of Stent Repositioning

*1000*

*1002*

Begin stent repositioning method

*1004*

Retrieve stent into delivery device.

*1006*

Reposition delivery device to desired location.

*1008*

Deploy stent at desired location.

*1010*

End stent repositioning method

Bladder Neck

Lateral lobar tissue

Apical lobar tissue

Veru

EUS

Bladder
Neck

Lateral lobar tissue

Apical lobar tissue

Veru

EUS

INTRALUMINAL STENTS FOR TREATING BENIGN PROSTATIC HYPERPLASIA

BACKGROUND

Benign prostatic hyperplasia (BPH) is a common benign condition that develops in men and is bothersome in elderly patients. In this condition, the prostate gland is enlarged and not cancerous. Benign prostatic hyperplasia is also called benign prostatic hypertrophy or benign prostatic obstruction.

The prostate gland is a fibromuscular and glandular organ lying just inferior to the bladder. As the prostate enlarges, the gland presses against and pinches the prostatic urethra. This leads to weakening the bladder and inability to completely empty the bladder. The narrowing of the prostatic urethra causes the symptoms observed with BPH. As many as 14 million men in the United States have lower UTI symptom, suggestive of BPH. Approximately half of all men over the age of 50 will develop an enlarged prostate. By the time men reach their 70's and 80's, approximately 85-90% of them will experience urinary symptoms from BPH.

While the etiology of BPH is not completely well-understood, it is thought to be multifactorial and endocrine controlled. BPH develops in the transitional zone of the prostatic urethra. Symptoms often include irritative and obstructive flow. Specifically, the following symptoms may be suggestive of BPH: urinary frequency, urinary urgency, trouble starting a urinary stream, retention, incontinence, nocturia, pain after ejaculation. Complications of BPH include bladder stone, urinary tract infection, hematuria, bladder decompensation, renal failure, and acute/chronic urine retention.

Pharmacologic approaches for treatment include use of alpha blockers such as phenoxybenzamine (non-selective), prazosin (short-acting), terazosin & doxazosin (long-acting), and tamsulosin, alfuzosin, and silodosin ($\alpha$1a) selective blockers. Additionally, 5$\alpha$-reductase inhibitors and combination therapies are also used. Pharmacologic approaches are inadequate in the effectiveness and often used as short-term treatments. Side-effects of pharmacologic approach include orthostatic hypotension, dizziness, tiredness, retrograde ejaculation, rhinitis, and headache.

Conventional and recent surgical therapies include a) Transurethral resection of the prostate (TURP), b) Transurethral incision of the prostate (TUIP), c) LASER therapy, d) Other forms of energies to vaporize the prostate, d) simple prostatectomy, e) Prostatic stents, and f) Urolift procedure. With TURP, endoscopic electrosurgical resection is used to alleviate symptoms and improve flow rate. However, TURP requires spinal or general anesthesia and a 4-6 week recovery time with at least 24 hours of catheterization. Additionally, some complications include impotence, incontinence, bleeding, retrograde ejaculation, and TUR syndrome (vomiting, nausea, confusion, hypertension, etc.). Simple prostatectomy may be performed when prostate gland is over 100 grams or when BPH occurs with a large vesical stone. With c) LASER therapy, LASER energy is used to ablate, vaporize, or enucleate the prostate, which has advantages such as minimal blood loss and the ability to be performed as an out-patient procedure. However, LASER therapy may require longer post-operative catheterization time and requires high cost of LASER fiber and generators. Other forms of energies including microwave, focused ultrasound, water-induced thermotherapy, electrovaporization, etc., have also been tried with variable outcomes. Transurethral balloon dilation of the prostate has also been tried in the past with poor outcomes. Prostatic stents (temporary and permanent) have also been employed in the past. Poor anchoring, migration of the stent, and difficult removal have led to poor outcomes/utilization. Recent developments include Urolift—a technique where the prostates are tied away from the urethra. While it is minimally invasive, the procedure still has some disadvantages such as use of a temporary catheter, questionable durability of outcome, and the chance of a painful/bothersome recovery for the patient.

SUMMARY

Some embodiments are directed to minimally invasive systems and methods for maintaining a patency of a body lumen. One non-limiting indication is treating benign prostatic hyperplasia (BPH). The device for such treatment can include a stent that is placed within the prostatic urethra. The device can be coated with PTFE, silicone, and/or other hydrophilic and/or hydrophobic coating materials. In some embodiments, the device can be coated with one or more therapeutic agents, including drugs such as alpha-1 blockers, 5 alpha-reductase inhibitors and combination therapies, such as in an extended-release coating. In some embodiments, a device is not coated with one or more therapeutic agents, such as a drug.

Some embodiments advantageously leverage the expansion of the prostatic urethra using devices including a stent having a radial force gradient along its longitudinal length. The stent can control and improve flow throughout the range of the urethra without interfering with the natural expansion and collapse of the urethra during evacuation. As such, the urethral stent can include various longitudinal zones or regions, each configured for specific clinical and anatomical requirements.

For example, a proximal region of the stent (nearest the internal urinary sphincter and bladder when implanted), sometimes referred to as the tail region, can be configured to provide a small amount, almost none, or no radial expansion force against the wall of the prostatic urethra. The proximal region can be configured with a plurality of atraumatic ends to anchor the stent within the prostatic urethra, and to prevent proximal migration of the stent (e.g., into or towards the bladder). A middle region of the stent, sometimes referred to as the body region, can be configured to provide a maximum amount of radial expansion force to maintain patency of the urethral lumen, or to counter the compressive force of an enlarged prostate that is compressing the prostatic urethra. The middle region of the stent can be positioned within the prostatic urethra, between the interior and exterior urinary sphincters. A distal region of the stent (nearest the external urinary sphincter when implanted) can be provided as a loop or droplet-shaped ring. The distal region may be configured to provide no radial expansive force against the prostatic urethra luminal wall. Instead, the distal region may serve as a connection point for delivery and retrieval of the stent. For example, a detachable member, such as a clamp, hook or forceps-like grasping member may releasably attach to the distal region to push the stent out of or to pull the stent into the working channel of a delivery catheter or scope (such as a cystoscope, etc.).

The stent may be constructed from any one or more of a variety of materials. For example, the stent may be constructed from shape-memory alloys (SMAs), flexible metals such as stainless steel, titanium, etc. or flexible polymers including shape memory polymers (SMPs). In some embodiments, the stent material may include coatings to prevent degradation and encrustation. The coating might be of hydrophobic or hydrophilic in nature such as silicone. In some embodiments, the coating could include PTFE or ePTFE. In some embodiments, the coating could include flexible silicones, hydrogels, mucoadhesive substrate, pressure-sensitive adhesives, and other suitable elastomers, such as synthetic rubbers. In one or more embodiments, a coating having a micropattern may include and/or be formed from a biologically-derived protein structure (e.g., collagen, etc.)

In some embodiments, disclosed is a method of implanting the urethral stent. An image-guided flexible cystoscope or a catheter with a camera can be utilized in combination with a mechanism to deploy, retrieve, and/or reposition the stent. The stent can be loaded into the flexible cystoscope from the scope's distal (output) end.

The stent can be customized or sized for a specific patient, including age, race, demographic, predispositions, urethral dimensions, prostatic dimensions, anatomical differences, and other factors unique to the patient. For example, the length of the stent or length of each region of the stent may be selected and configured to match the patient's particular anatomical dimensions.

In some embodiments, a device can include any combination of the following features, or others as disclosed herein.

BRIEF DESCRIPTION OF THE DRAWINGS

FIG. 8 is a flow chart illustrating one method of deploying a urethral stent.

DETAILED DESCRIPTION

Figure 1:
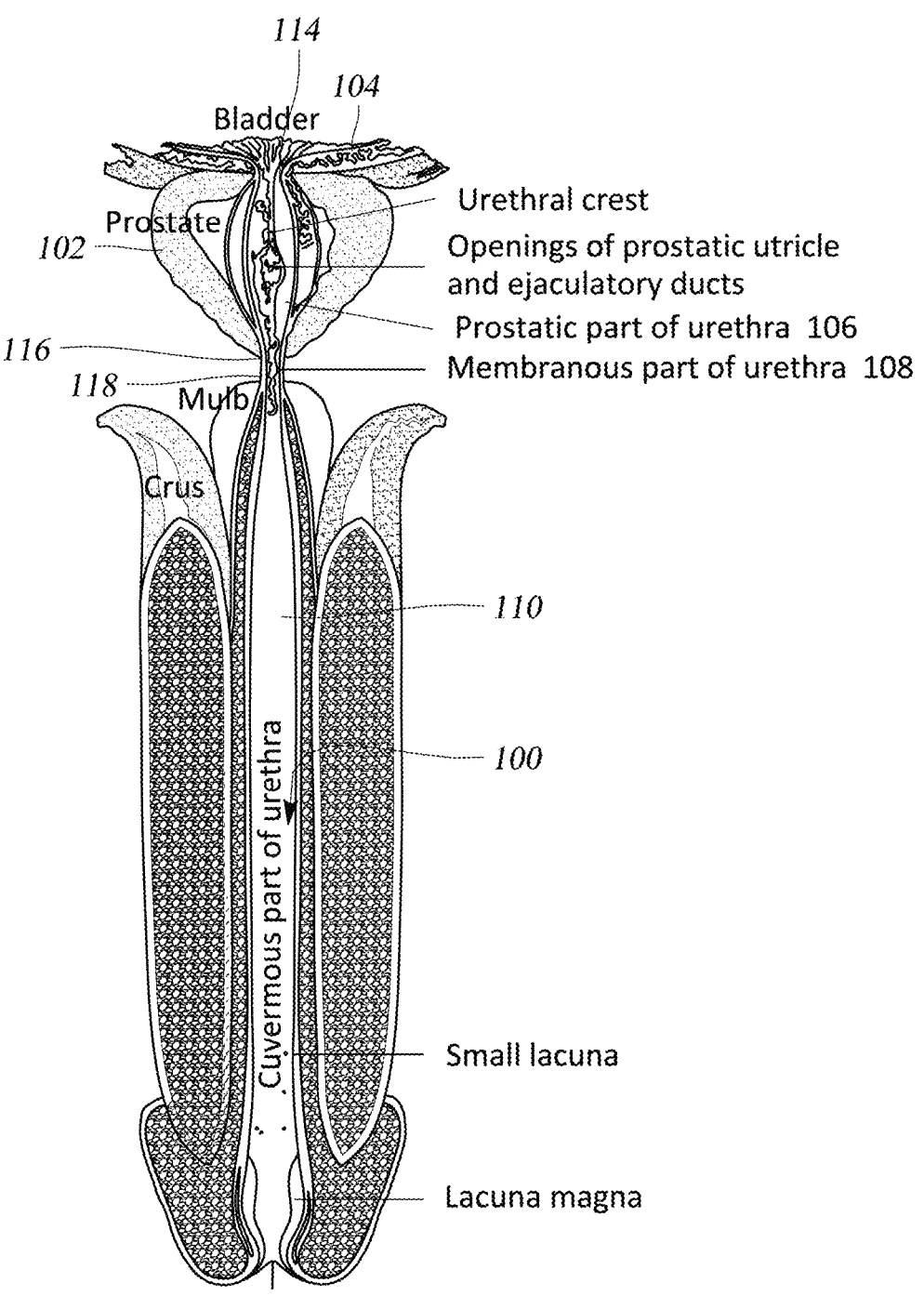
FIG. 1 illustrates a cross-sectional view of a male urethra and associated anatomy.

Several factors influence the onset and progression of BPH (Benign Prostate Hyperplasia, also known as Benign Prostate Hypertrophy). The most common factor is aging and the shift in hormonal balance. FIG. 1 illustrates the cross-section of the male urethra 100 in detail. The prostate 102 is shown right below the bladder 104. The region of urethra 100 surrounded by the prostate 102 is the prostatic urethra 106, which is bounded by the bladder 104 opening proximally and the membranous urethra 108 distally. At the membranous part of the urethra 108, the urethra 100 becomes the cavernous (penile) urethra 110 and continues to and ends at the external urethral orifice 112. An internal urinary sphincter (not shown) is located at and surrounds the junction between the bladder 104 and the proximal end 114 of the prostatic urethra 106. The internal urinary sphincter (not shown) controls the flow of fluid from the bladder 104 into the prostatic urethra 106. An external urinary sphincter (not shown) is located at the membranous part of the urethra 108. The external urinary sphincter (not shown) surrounds the junction between the distal end 116 of the prostatic urethra 106 and the proximal end 118 of the penile urethra 110.

Figure 2:
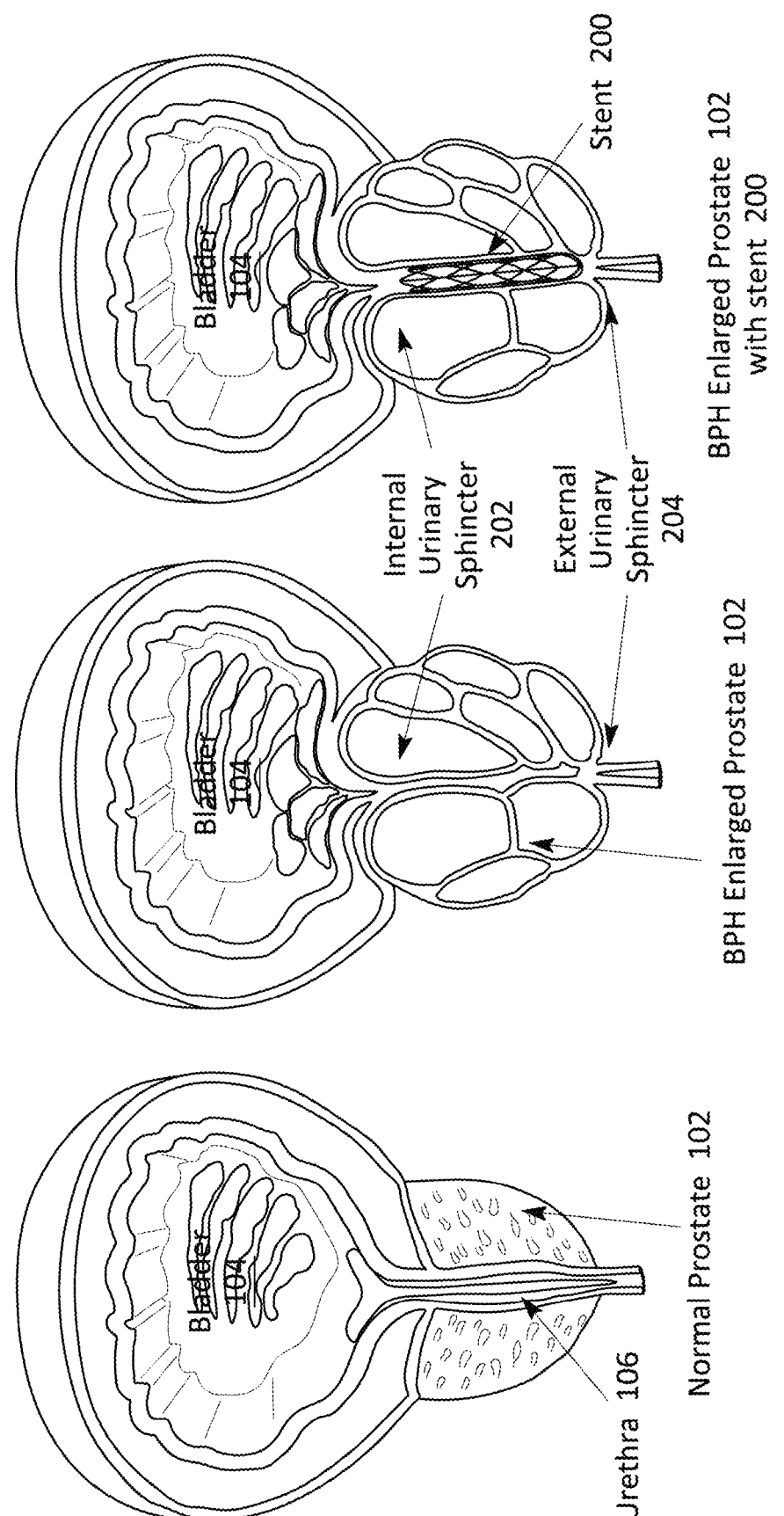
FIG. 2 shows a schematic cross-section of the prostatic urethra and the bladder in the case of a healthy prostate, an enlarged prostate, and an enlarged prostate with a urethral stent positioned within the prostatic urethra.

As illustrated in FIG. 2, the prostatic urethra 106 is compressed to a reduced diameter when the prostate 102 is enlarged. This leads to the various symptoms observed in the progression of BPH, including but not limited to urinary frequency, urgency, nocturia, hesitancy, weak stream, straining, and prolonged voiding. An implanted device 200 for overcoming the symptoms of BPH is also shown in FIG. 2. The implanted device 200 is a urethral stent that is located entirely within the prostatic urethra 106, between the internal urinary sphincter 202 and the external urinary sphincter 204.

Disclosed herein are devices, including stents that can be configured to adjust the diameter and opening of the prostatic urethra. Prostatic urethral stents can include various generally prosthetic devices, including tubular members configured to maintain or improve the patency of at least a portion of the urethra, such as the prostatic urethra. In some embodiments, a device can improve the patency of the prostatic urethra, but not the membranous urethra or penile urethra.

Figure 3:
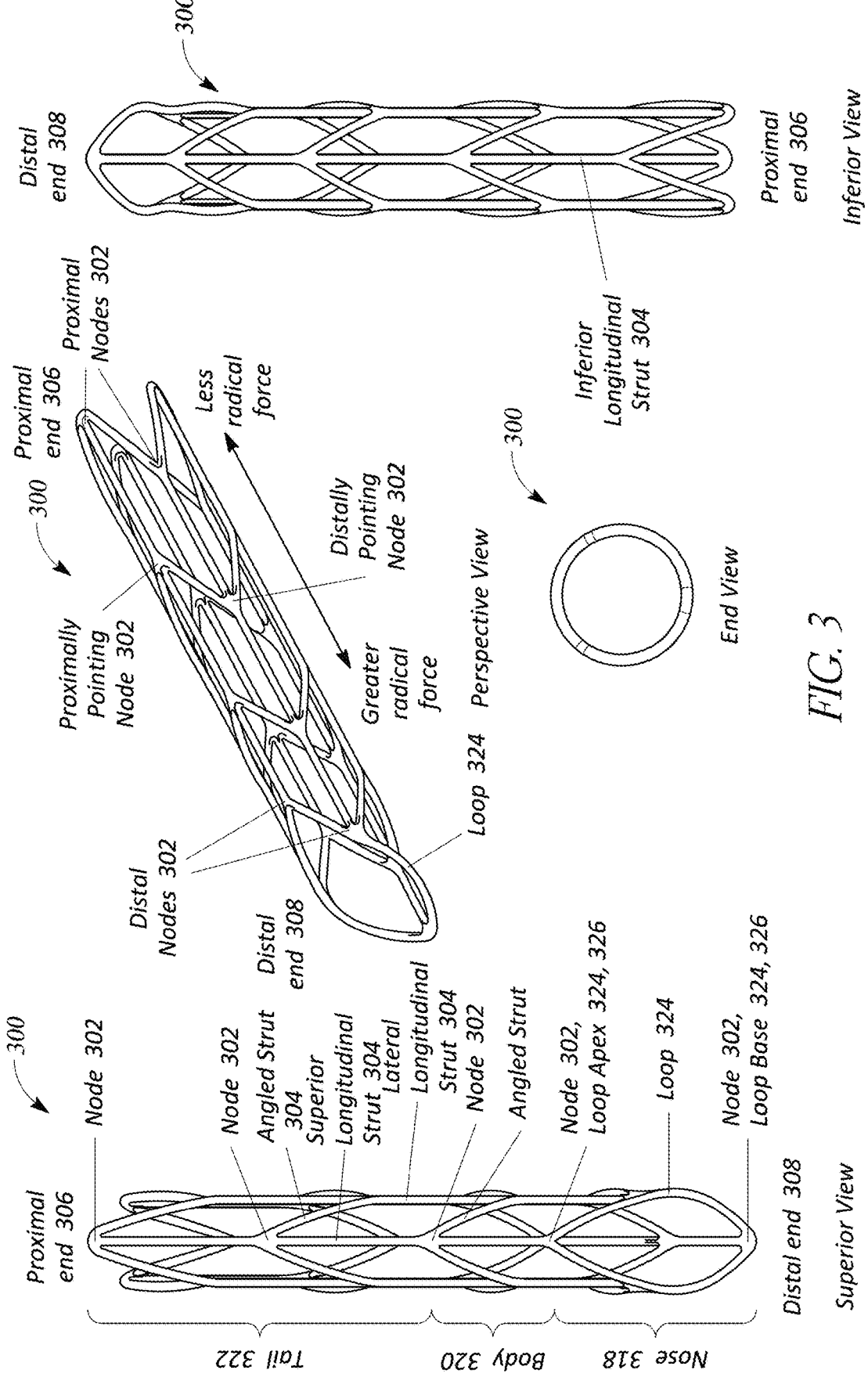
FIG. 3 illustrates a urethral stent configured to be positioned within the prostatic urethra, as shown in FIG. 2.

FIG. 3 illustrates various views of one such device in the form of a urethral stent 300. The urethral stent 300, or stent 300, is formed in a generally cylindrical shape from a plurality of nodes 302 and struts 304. In one embodiment, the nodes 302 and struts 304 are formed by cutting material away from a cylindrical member. The nodes 302 may be generally triangular or arrowhead shaped and may point either towards the stent's proximal 306 or distal 308 end. Nodes 302 connect longitudinal struts 310 and angled struts 312 to each other to form parallelogram, trapezium, and/or quadrilateral-shaped cells. The acute angles formed between longitudinal struts 310 and angled struts 312 of a particular cell may be equal or decrease in magnitude moving from cell to cell in the proximal direction. For example, the acute angles formed between longitudinal struts 310 and angled struts 312 of a cell in the stent's body region 320 may be larger than the acute angles formed between longitudinal and angled struts of the cells in the stent's tail region 322. In some embodiments, the longitudinal lengths of the cells increase moving along the longitudinal axis of the stent 300 in the proximal direction (towards the stent's proximal end 306).

Adjacent circumferentially positioned cells form longitudinal regions of the urethral stent 300. For example, the illustrated stent of FIG. 3 includes nose, body, and tail regions 318, 320, 322. Each region 318, 320, 322 is configured for a particular clinical and anatomical function, as described further below.

The nose region 318 of the stent 300 is located at the stent's distal end 308. The struts at the nose region 318 are formed into a loop 324. The loop 324 may be used to attach to a deployment and/or retrieval member (not shown) that may be used to push and/or pull the stent 300 out of and/or into the working lumen of a deployment device. Pulling on the loop 324 (in the distal direction, away from the bladder when implanted) causes a lever action and compression of the stent 300 into a collapsed position so it may be drawn into the working channel of a deployment device (e.g., a catheter, cystoscope, etc.).

The nose region 318 of the stent 300 also allows a clinician to rotationally orient the stent 300 about its longitudinal axis. For example, the base 326 of the loop 324 is generally positioned at and aligned with the longitudinal struts extending along the inferior surface of the stent. The apex 328 of the loop is generally positioned at and aligned with the longitudinal struts extending along the superior surface of the stent 300. The shape of the loop 324 allows a clinician to orient the stents superior and inferior surfaces with the anatomy of the patient's urethra.

The outward radial force provided by the stent 300 generally decreases along the stent's proximal direction. The urethral stent 300 is more collapsible in the stent's 300 proximal direction (towards the bladder, when implanted). For example, the stent 300 may be characterized by a collapsibility gradient. The body region 320 of the stent 300 provides the greatest radial force and therefore, the least collapsibility when implanted within the prostatic urethra. The tail region 322 of the stent provides the least radial force, and therefore the greatest collapsibility when implanted within the prostatic urethra.

The body region 320 of the stent 300 provides enough radial force to counter or partially counter compressive forces on the prostatic urethra from an enlarged prostate, such as a prostate of an individual suffering from BPH. The force outward radial force provided by the stent's body region 320 helps the prostatic urethra stay open during evacuation of the bladder.

The tail region 322 of the stent 300 provides minimal radial force so as not to interfere with the body's control over the opening and closing of the internal urinary sphincter located at the proximal portion of the prostatic urethra. The tail region may provide just enough outward radial force to cause the proximal nodes 302 located at the stent's proximal end 306 to expand slightly outward and to engage the soft tissue of the prostatic urethra near or at the internal urinary sphincter. The proximal nodes 302 may act as atraumatic anchors that contact the prostatic urethra to prevent proximal (bladder-direction) migration of the stent 300 once implanted.

The stent 300 may be sized to match the patient's particular anatomy. For example, the length of the patient's prostatic urethra may be determined, and then a urethral stent 300 having a length equal to or less than the prostatic urethra length may be selected. In one embodiment, the length of the stent 300 is determined by the length of the stent's tail region 322. In other words, stents 300 of different length may have the same nose and body regions 318, 320, but different tail regions 322. For example, the longer stent's tail region 322 may be formed of longer struts 304 or it may include more cells than the shorter stent's tail region 322.

Figure 4:
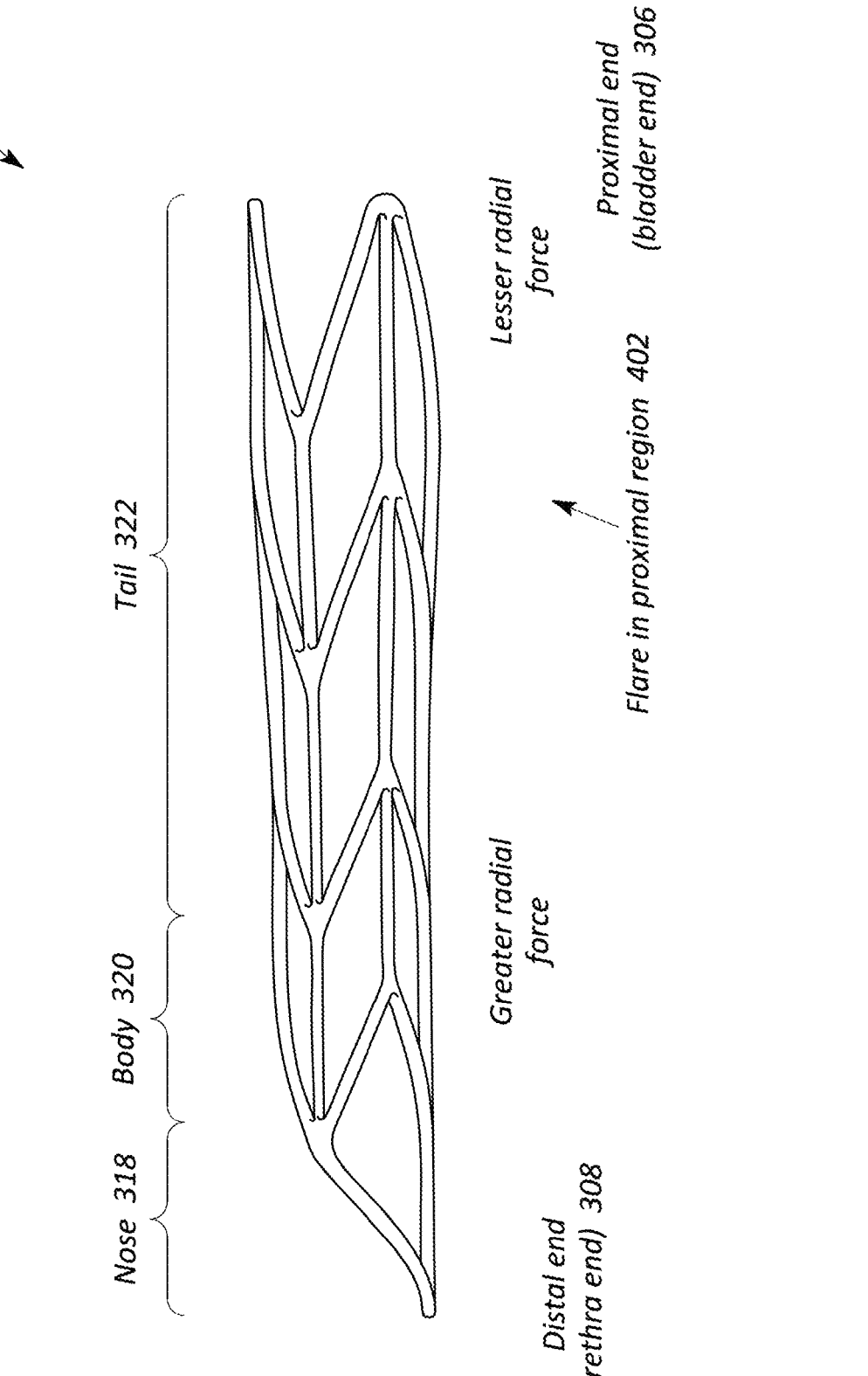
FIG. 4 illustrates another urethral stent having a flared proximal region, also configured to be positioned within the prostatic urethra, as shown in FIG. 2.

FIG. 4 shows another embodiment of a urethral stent 400. The stent 400 of FIG. 4 is similar to the stent 300 of FIG. 3, except that the stent 400 of FIG. 4 has a flared proximal portion 402 of its tail region 322. For example, the outer and inner diameters of the proximal portion of the tail 322 may be larger than the distal portion of the tail 322. In some embodiments, the outer and inner diameters of the stent 400 increase gradually and/or uniformly along the stent's 400 proximal direction. The flared region 402 of the stent may be obtained by placing the stent 400 on a mandrel or other device to shape the stent 400.

Figure 5:
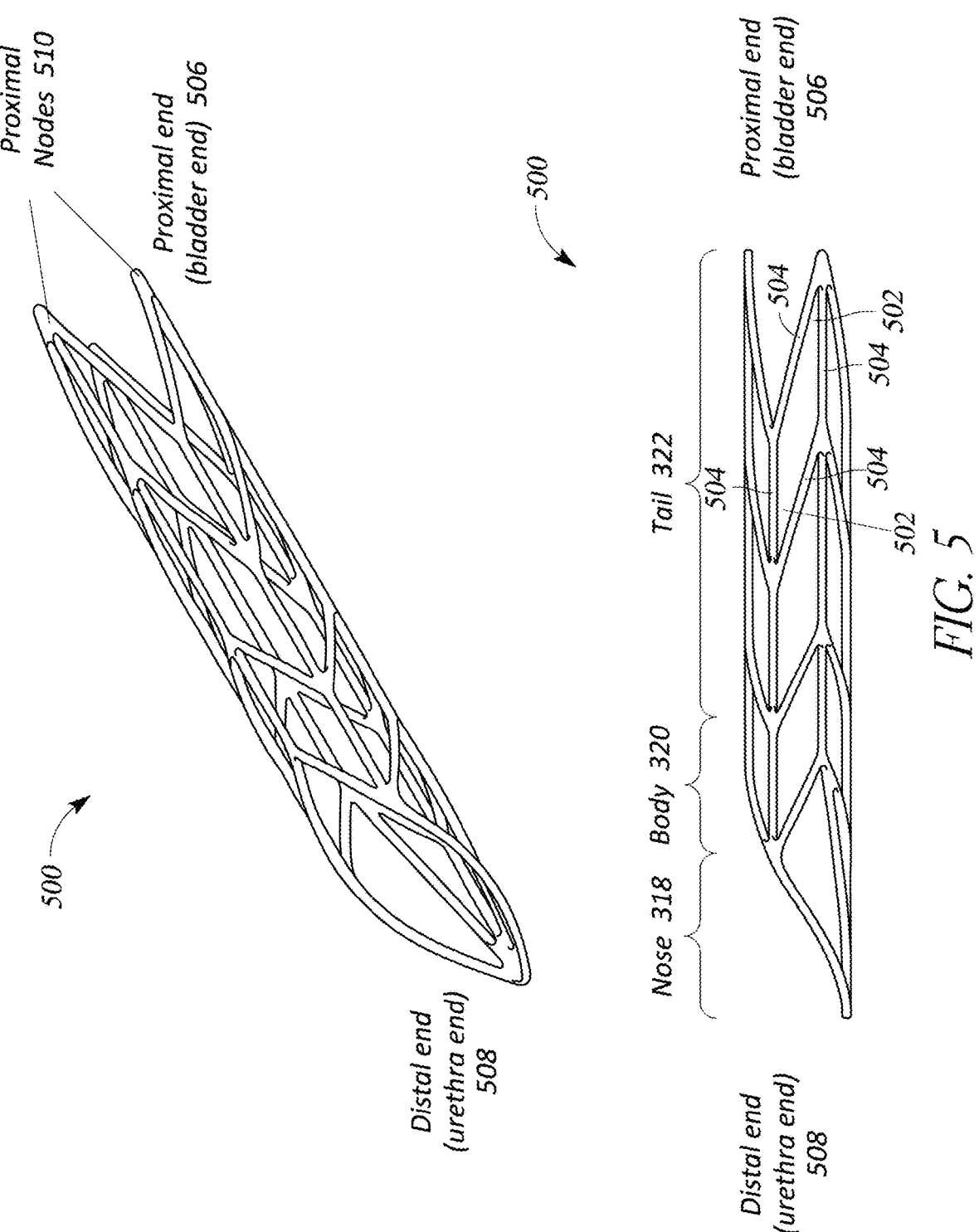
FIG. 5 illustrates another urethral stent having a longer proximal end and pointier atraumatic ends formed from more acute internal angles, also configured to be positioned within the prostatic urethra, as shown in FIG. 2.

FIG. 5 shows yet another embodiment of a urethral stent 500. The stent 500 of FIG. 5 is also similar to the stent 300 of FIG. 3, but includes smaller acute angles 502 between struts 504, particularly at the stent's 500 proximal end 506. The proximal nodes 510 at the very proximal end 508 of the stent 500 are pointier than the proximal nodes of the stents 300, 400 of FIGS. 3 and 4, as well.

Figure 6:
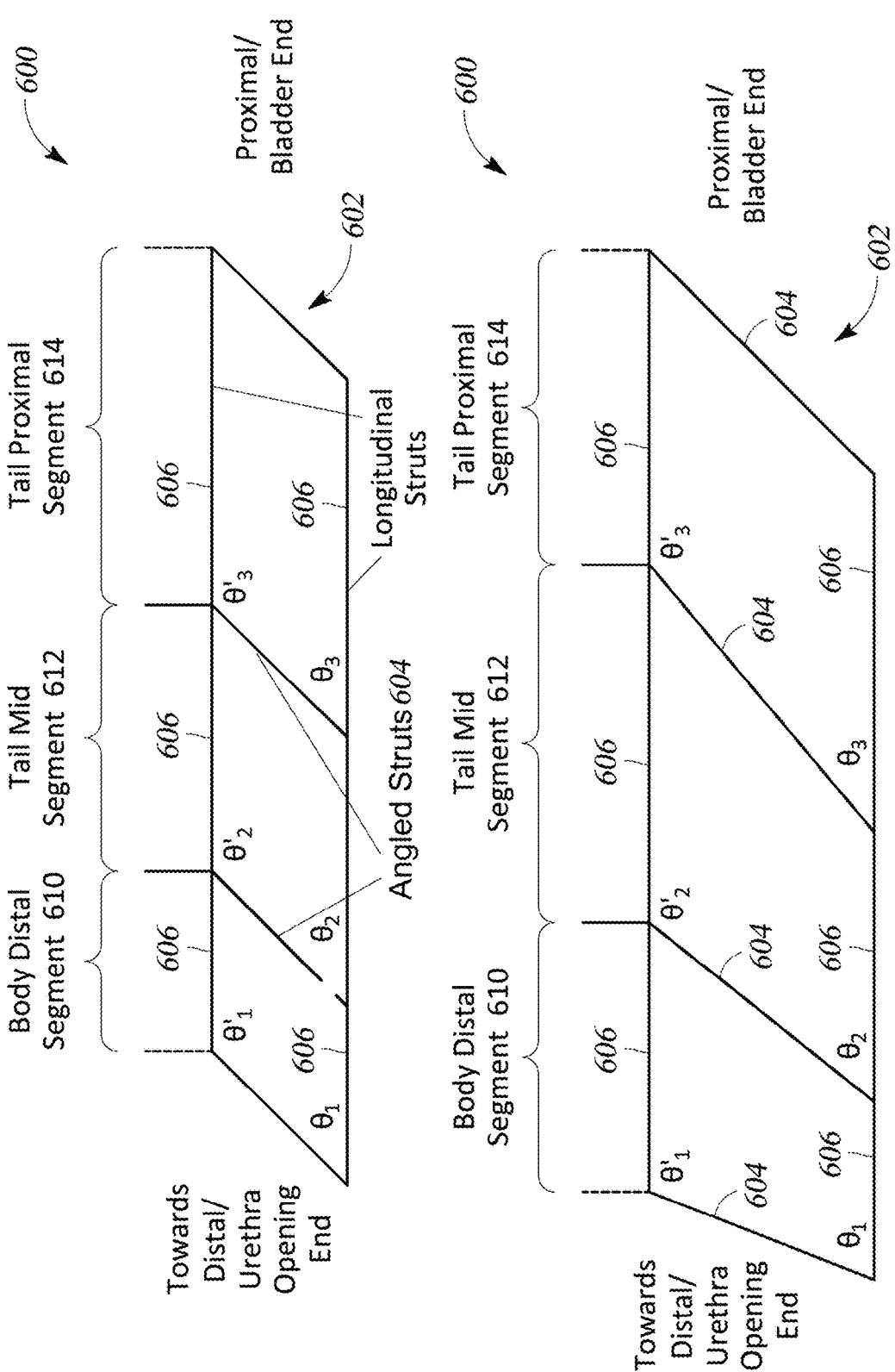
FIG. 6 is a schematic representing one example of the cell geometry of one or more urethra stents, including but not limited to, the urethral stents of FIGS. 2-5.

FIG. 6 shows a schematic of the cells 602 of a urethral stent 600 according to various embodiments. In one embodiment, as shown in the upper figure, each cell 602 is formed as a parallelogram. In the illustrated embodiment, the angled struts 604 of longitudinally adjacent cells 602 have the same length, and the longitudinal struts 606 of each cell 602 have the same length. The longitudinal strut 606 lengths increase or stay the same moving in the stent's proximal direction (toward the bladder when implanted). For example, the lengths of the longitudinal struts 606 in the stent's body distal 610 segment are the same, the lengths of the longitudinal struts 606 in the stent's tail mid segment 612 are the same, and the lengths of the longitudinal struts 606 in the stent's tail proximal segment 614 are the same. The acute angles $\theta_1$, $\theta_2$, $\theta_3$, of the cells 602 are the same and the obtuse angles $\theta'_1$, $\theta'_2$, $\theta'_3$ of the cells 602 are also the same.

In the embodiment shown in the lower figure of FIG. 6, each cell 606 is formed as a trapezium, or irregular quadrilateral. In the illustrated embodiment, the angled struts 604 of longitudinally adjacent cells 602 have different lengths, and the longitudinal struts 606 of each cell 602 also have the different lengths. The longitudinal strut 606 lengths increase or stay the same moving in the stent's proximal direction (toward the bladder when implanted). For example, the length of the upper longitudinal strut 606 in the stent's body distal segment 610 is longer than the lower longitudinal strut 606 in the stent's body distal segment 610. Similarly, the length of the upper longitudinal strut 606 in the stent's tail mid segment 612 is longer than the lower longitudinal strut 606 in the stent's tail mid segment 612, and the length of the upper longitudinal strut 606 in the stent's tail proximal segment 614 is longer than the lower longitudinal strut 606 in the stent's tail proximal segment 614. The acute angles $\theta_1$, $\theta_2$, $\theta_3$, of the cells decrease along the stent's 600 proximal direction and the obtuse angles $\theta'_1$, $\theta'_2$, $\theta'_3$, of the cells increase along the stent's 600 proximal direction. The radial force provided by the stent 600 at each segment (e.g., body distal, tail mid, and tail proximal segments 610, 612, 614) may be controlled by controlling one of more of the acute angles, obtuse angles, and strut lengths of the cells 602. In some embodiments, the acute angles $\theta_1$, $\theta_2$, $\theta_3$, of the cells 602 increase along the stent's proximal direction and the obtuse angles $\theta'_1$, $\theta'_2$, $\theta'_3$, of the cells 602 decrease along the stent's 600 proximal direction The angle values and/or relative values may be selected depending upon the amount of outward radial force desired in a particular region. For example, the acute and/or obtuse angles may include a combination of constant, decreasing or increasing, and then decreasing angle values.

Figure 7:
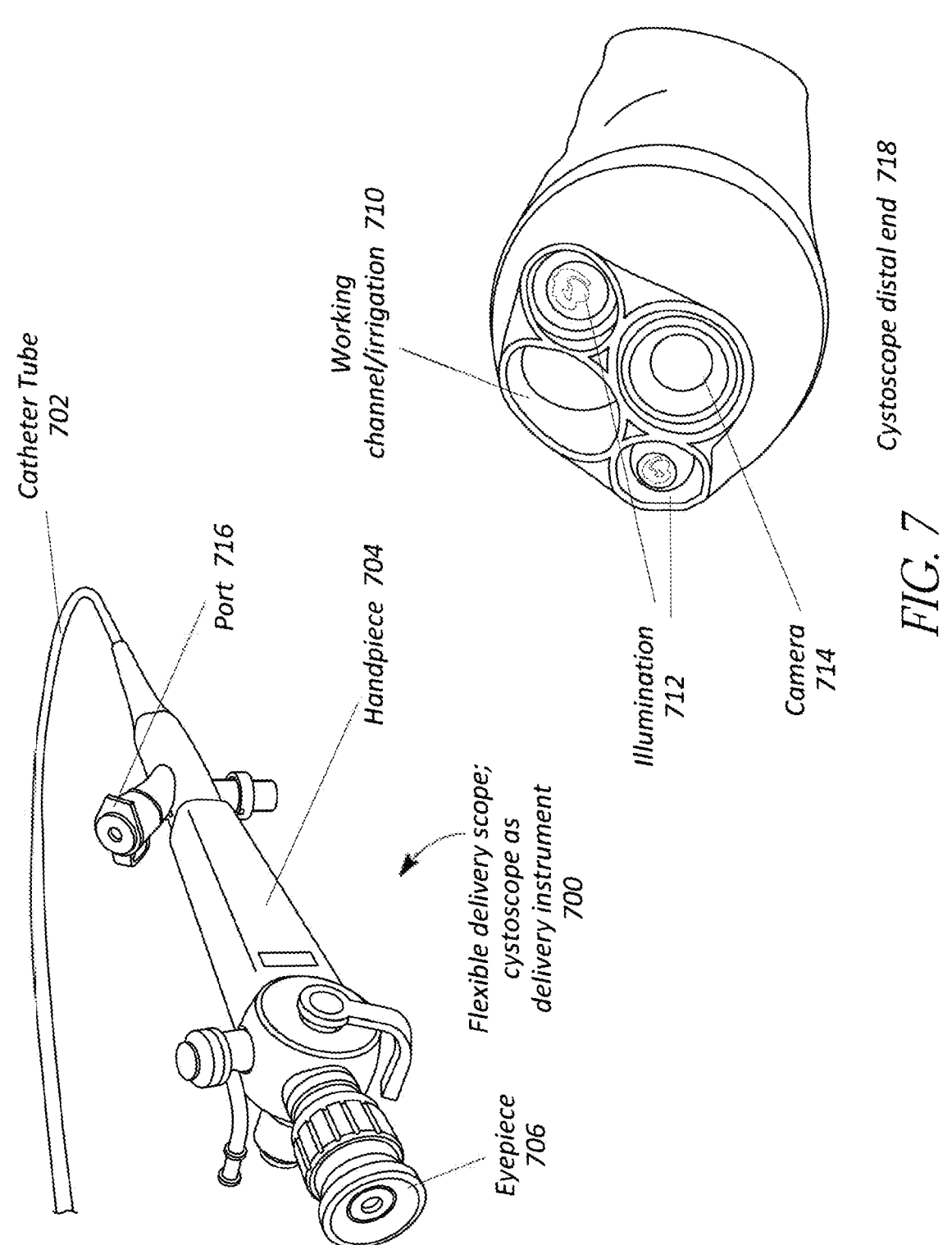
FIG. 7 illustrates one embodiment of a delivery device suitable for delivering a urethral stent, such as the urethral stents of FIGS. 2-6.

FIG. 7 illustrates one embodiment of a delivery device 700 suitable for delivering any of the urethral stents described herein. In the illustrated embodiment, a cystoscope is provided. The cystoscope includes a catheter tube 702 that terminates at a handpiece 704. An eyepiece 706 is located at the handpiece's proximal end 708. The catheter tube 702 includes a plurality of channels 710, 712, 714. In the illustrated embodiment, the catheter tube 702 includes a working channel 710, two illumination channels 712, and a camera channel 714. The eyepiece 706 is optically coupled to the camera 714 so the operator may visualize the interior of the lumen into which the catheter tube 702 has been inserted. A port 716 is fluidly coupled to the working channel 710 to provide irrigation, aspiration, access to a control wire located in the working channel 710, etc.

The urethral stent (not shown) may be loaded into the working channel 710 of the delivery device 700 by first attaching a detachable control member to the stent's nose portion. For example, the control member may include a hooked wire, a wire with releasable clasp, etc. for detachable coupling to the stent. The stent may be connected to the control member at the control member's distal end. The proximal end of the control member may be fed through the delivery device's working channel 710 in a retrograde direction such that the control member enters the catheter tube 702 at the working channel distal end 718 and exits the catheter tube at the port 716. The stent may be loaded into the distal end 718 of the working channel 710 by pulling it nose-first into the working channel's distal 718 end using the control member. The pulling force will cause the stent to collapse as it contacts and presses against the inside perimeter of the working channel 710 lumen. When loaded, the proximal end of the stent (the end that will be adjacent the bladder when implanted) will be flush with or set back (proximally) from the distal end 718 of the delivery device's working channel. The delivery device 700 may be used to deliver, retrieve, and/or reposition the stent with respect to the prostatic urethra, as follows.

FIG. 8 is a flow chart illustrating one embodiment of a method 800 of deploying a urethral stent, such as any of the stents described herein, in the prostatic urethra. A delivery device, such as the delivery device of FIG. 7 or any other delivery device, is provided. A urethral stent, such as any of the stents described herein, is loaded into and positioned near the distal end of the delivery device's catheter.

The method 800 begins at block 802. At block 804, the delivery device is advanced through the urethra in a proximal direction towards the bladder. The delivery device is advanced until the distal end of the catheter is within the bladder. At block 806, the proximal segment or a portion of the tail segment of the stent is deployed by advancing the control member with respect to the delivery device, which results in partially pushing the stent out of the delivery device's working channel and into the bladder. The deployed portion of the tail segment expands within the bladder. At block 808, the delivery device and control member may be secured together and retracted in the distal direction, away from the bladder, until the proximal end of the proximal segment of the stent exits the bladder and is positioned at the proximal prostatic urethra. The remaining length of the stent may then be pushed out of the working channel as the scope is carefully withdrawn. At block 810, the control member may then be decoupled from the stent nose segment, and the control member and the delivery device may then be retracted distally and withdrawn from the urethra, leaving the stent positioned within the prostatic urethra. The length of the stent is selected so the stent is positioned only within the prostatic urethra, between the exterior and interior urinary sphincters. The method 800 ends at block 812.

Figure 9:
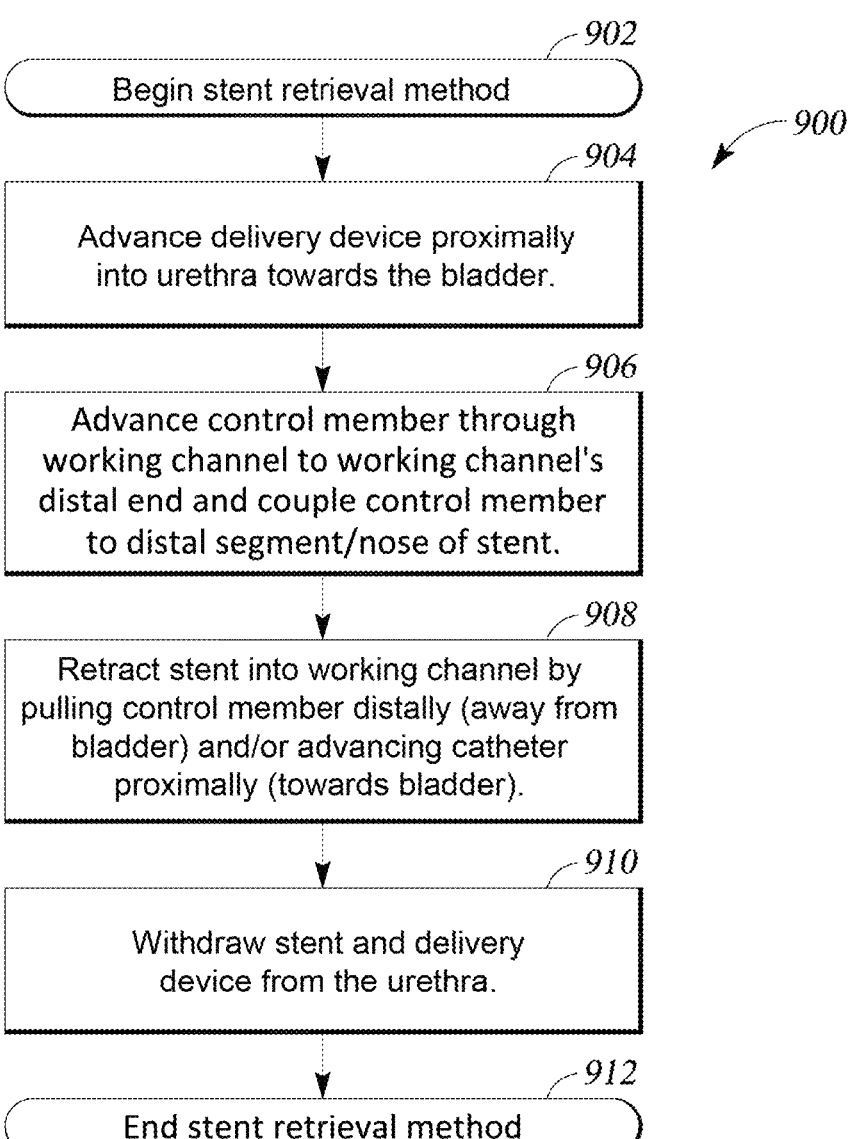
FIG. 9 is a flow chart illustrating one method of retrieving a urethral stent.

FIG. 9 is a flow chart illustrating one embodiment of a method 900 of retrieving a urethral stent, such as any of the stents described herein, in the prostatic urethra. A delivery device, such as the delivery device of FIG. 7 or any other delivery device, is provided. A urethral stent, such as any of the stents described herein, is located within a patient's prostatic urethra.

The method 900 begins at block 902. At block 904, the delivery device is advanced through the urethra in a proximal direction towards the bladder. The delivery device is advanced until the distal end of the catheter is adjacent or near the distal end/nose segment of the stent. At block 906, a control member is advanced though the delivery device's working channel to the working channel's distal end. The control member is attached to the stent nose segment. At block 908, the control member is then withdrawn in a distal direction (towards the delivery device's proximal end), thereby pulling the control member and the stent into the delivery device's working channel. Alternatively, or in addition, the delivery device may be advanced proximally (towards the bladder) to capture the stent within the delivery device's working channel. Contact between the working channel inside perimeter and the stent causes the stent to collapse radially as it is moves distally and into the working channel. Once the stent has been captured partially or completely within the working channel, at block 910 the stent and delivery device may be withdrawn and removed from the urethra. The method 900 ends at block 912.

Figure 10:
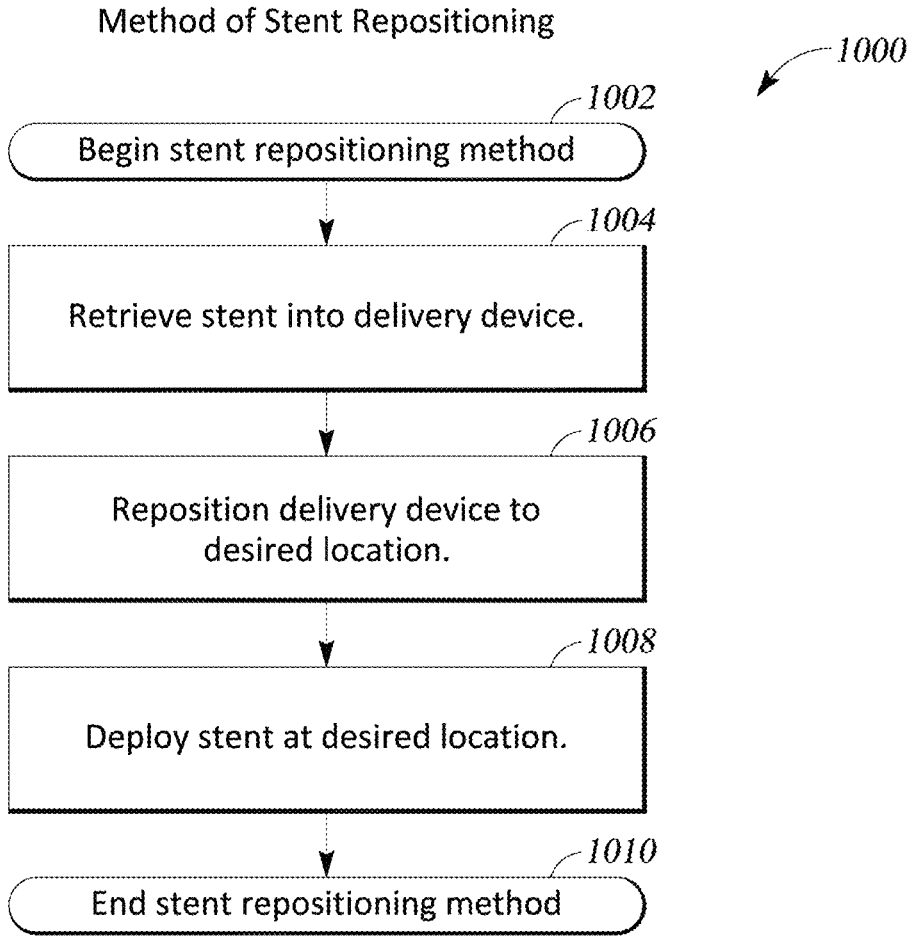
FIG. 10 is a flow chart illustrating one method of repositioning a urethral stent.

FIG. 10 is a flow chart illustrating one embodiment of a method 1000 of repositioning a urethral stent, such as any of the stents described herein, in the prostatic urethra. A delivery device, such as the delivery device of FIG. 7 or any other delivery device, is provided. A urethral stent, such as any of the stents described herein, is located within a patient's prostatic urethra.

The method 1000 begins at block 1002. At block 1004, the stent is initially retrieved into the working channel of a delivery device, for example, according to the method described above with respect to FIG. 9. At block 1006, the delivery device and captured stent are then repositioned to a new desired location. For example, the delivery device and stent may be positioned at the proximal prostatic urethra, or at any other desired location. At block 1008, the stent is then deployed, for example, according to the method described above with respect to FIG. 8.

Figure 11:
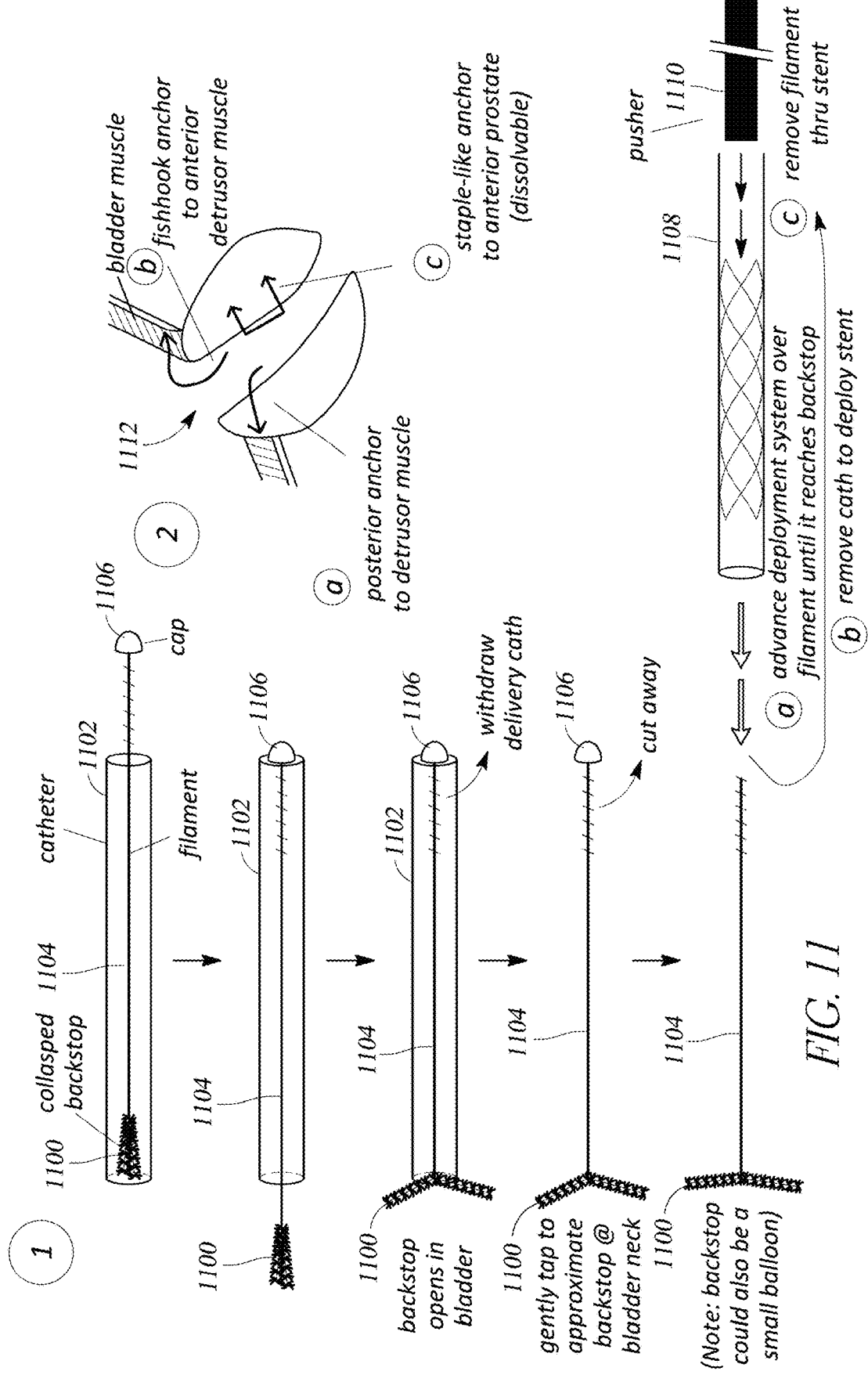
FIG. 11 illustrates a device for deploying a backstop prior to urethral stent deployment and device for anchoring a urethral stent.

FIG. 11 illustrates one embodiment of a system for deploying a backstop 1100 that may be used to deploy the stent or other device at a target location. The backstop 1100 is collapsed and positioned within a catheter 1102. A filament 1104 coupled is coupled to the backstop at one end and a cap 1106 at the filament's other end. The catheter 1102 is advanced within the urethra to a desired location, such as the proximal prostatic urethra. The catheter 1102 is withdrawn with respect to the filament 1104, causing the backstop 1100 to deploy and open within the bladder. The filament 1104 may be manipulated to position the backstop 1100 at the bladder neck. The cap 1106 is removed such that a stent delivery device 1108 may be advanced over the filament until it reaches the backstop. The delivery device 1108 is then withdrawn to deploy the stent. A pusher 1110 or control member may be used to hold the stent in position while the delivery device 1108 is withdrawn from the urethra. The backstop 1100 and filament 1104 may be removed by pulling the filament 1104 and backstop 1100 through the stent and through the urethra, until they exit the urethra.

The backstop 1100 may be a membrane, balloon or any other material that can expand and collapse in response to longitudinal force, and which can prevent movement of the stent into the bladder during deployment.

FIG. 11 also illustrates an anchoring mechanism 1112 that may be used to anchor the stent to the detrusor muscle, bladder muscle, or anterior prostate. The anchoring mechanism 1112 may be in the form of a staple. The anchoring mechanism 1112 may be dissolvable, as well.

Figure 12:
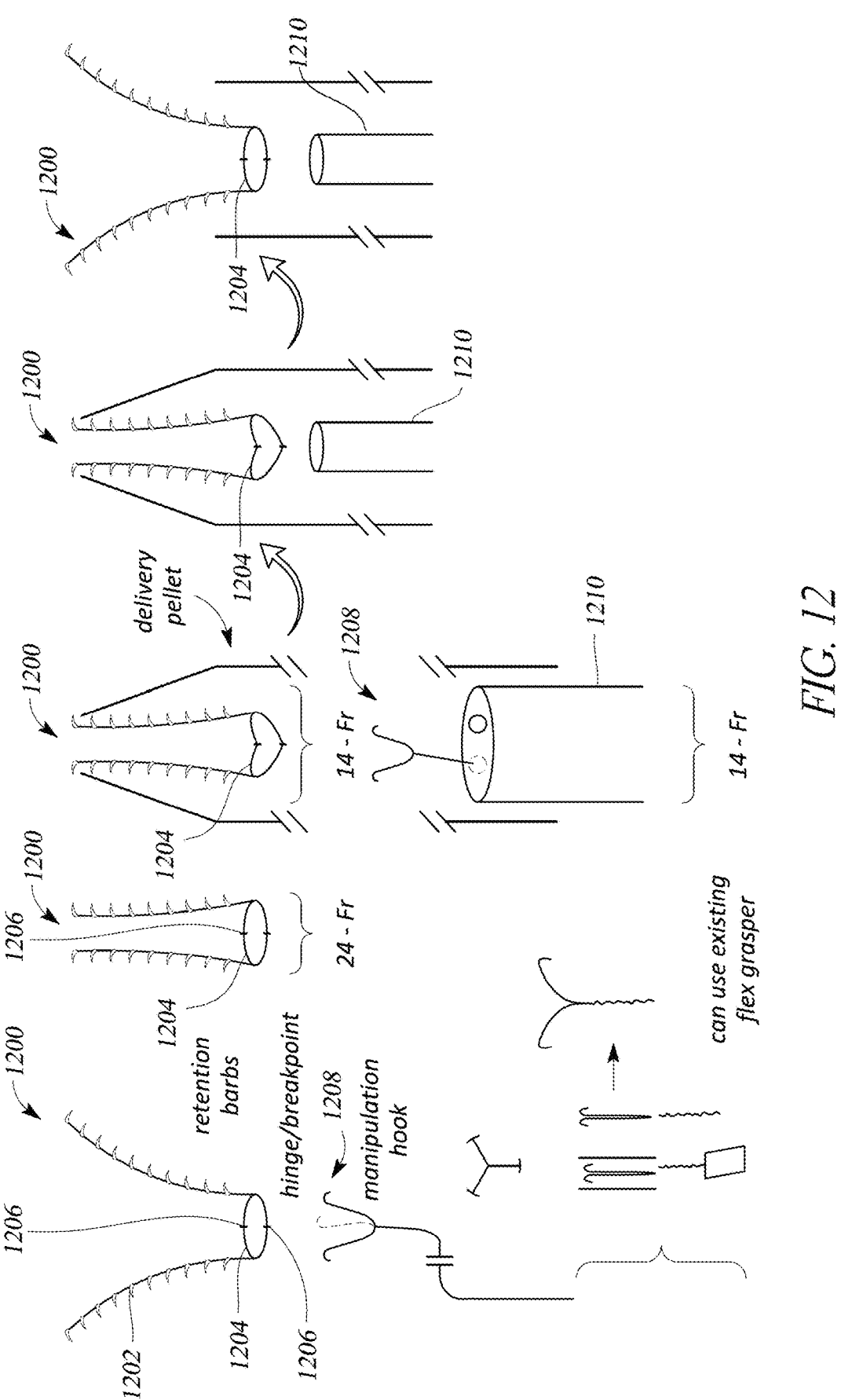
FIG. 12 illustrates a collapsible device for implantation within the prostatic urethra.

FIG. 12 illustrates a collapsible stent 1200 with deployment and retention components 1202. A distal ring (e.g., nose segment) 1204 of the stent 1200 includes a hinge/breakpoint 1206 that allows the stent 1200 to collapse to a smaller diameter. Retention barbs 1202 oriented in the proximal direction (pointing towards the bladder) prevent migration of the stent 1200 in the proximal direction (towards the bladder) but allow the stent 1200 to be freely advanced in the distal direction for removal or repositioning.

A manipulation hook 1208 may be attached to the distal ring 1204 to draw the stent 1200 into a catheter 1210. In one embodiment, the stent 1200 may collapse from a size 24 Fr diameter such that it can fit within a catheter 1210 having a 14 Fr inside diameter. The retention barbs 1202 and stent sizes may be used with or correspond to the sizes of any of the stents described herein.

Figure 13:
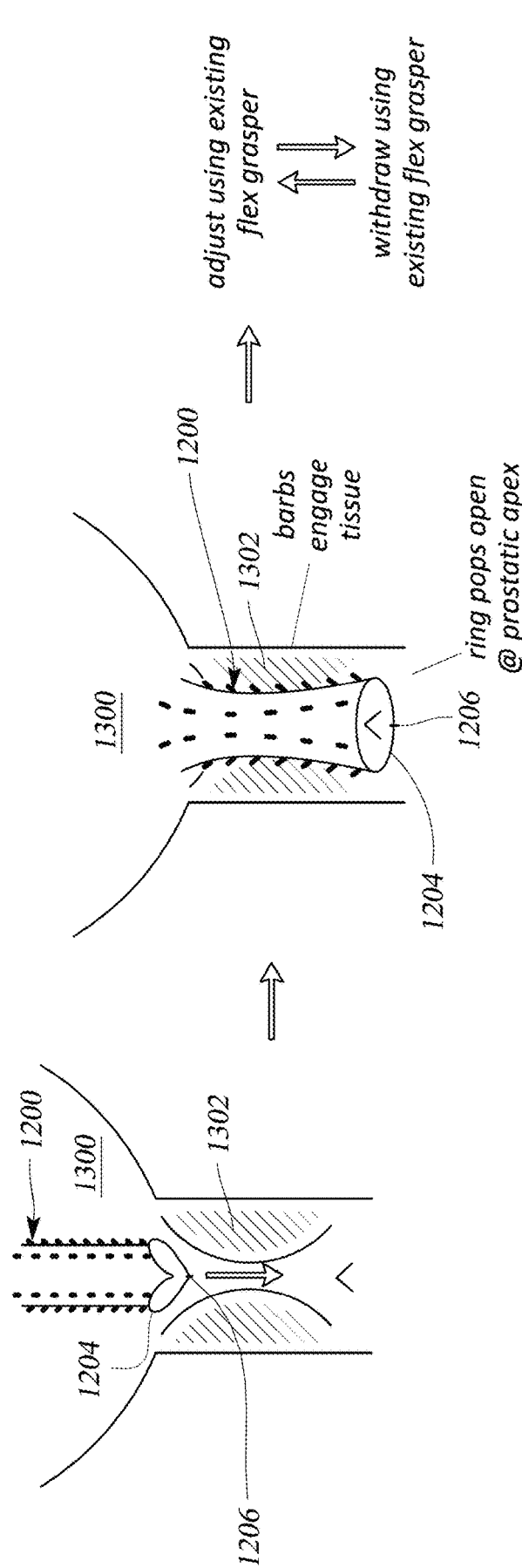
FIG. 13 illustrates the deployment of a device within the prostatic urethra.

FIG. 13 illustrates on embodiment of deploying the stent 1200 of FIG. 12. The stent 1200 is advanced into the bladder 1300 and then withdrawn distally into the prostatic urethra 1302. Barbs 1202 on the stent 1200 engage the luminal wall of the prostatic urethra 1302. A distal ring 1204 (e.g., nose segment) pops open at the prostatic apex. The position of the stent 1200 may be adjusted using flexible graspers (e.g., a flexible cystoscope grasper). Similarly, the stent 1200 may be removed from the urethra 1302 by withdrawing it distally out of the urethra 1302 using a flexible grasper.

FIGS. 14-22 illustrate additional embodiments of a urethral stent suitable for use according to any of the methods described herein. The illustrated embodiments demonstrate that the stent wall pattern may be consistently patterned with repeating, similar shaped cells, or the stent may include cells of different shapes in different regions. In addition, the cell shape may be any polygon, including a four-sided rhombus, or other quadrilateral. In some embodiments, the stent may include cells having three sides, five sides, or greater than five sides.

Figure 14:
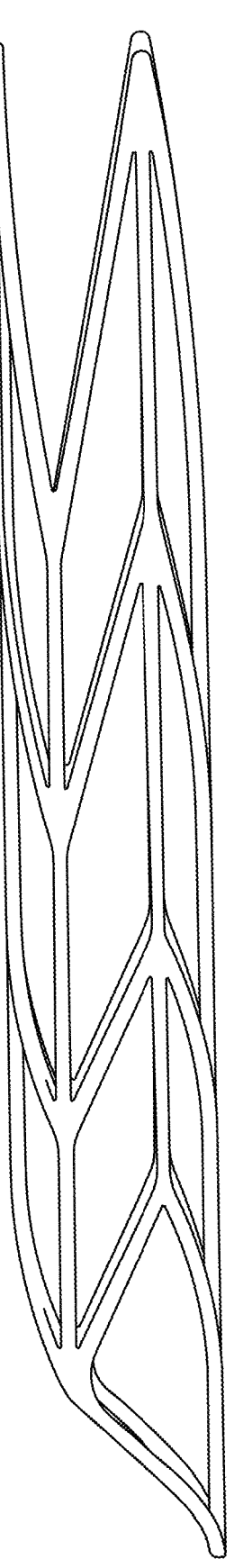
FIGS. 14-16 illustrates another embodiment of a urethral stent configured to be positioned within the prostatic urethra, as shown in FIG. 2.
Figure 15:
Figure 16:
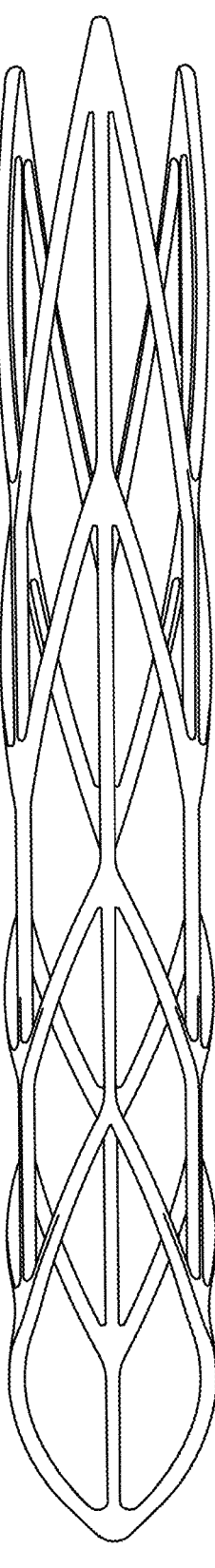
Figure 17:
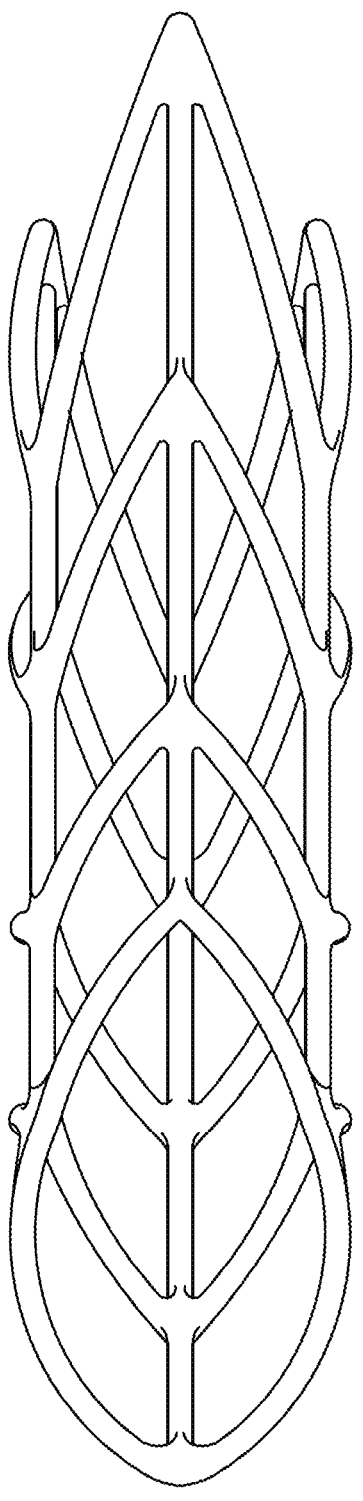
FIG. 17 another embodiment of a urethral stent configured to be positioned within the prostatic urethra, as shown in FIG. 2.
Figure 18:
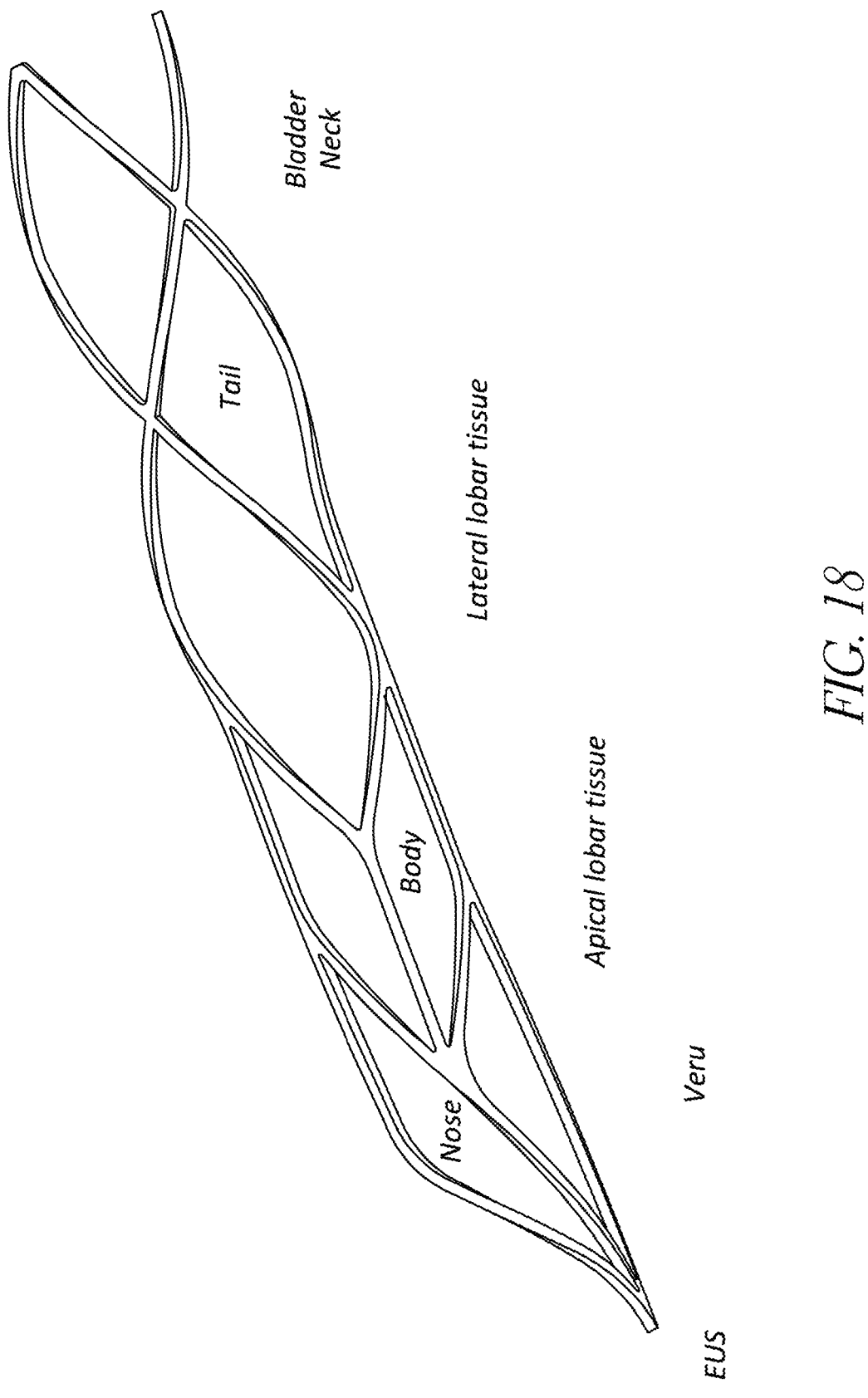
FIG. 18 another embodiment of a urethral stent configured to be positioned within the prostatic urethra, as shown in FIG. 2.
Figure 19:
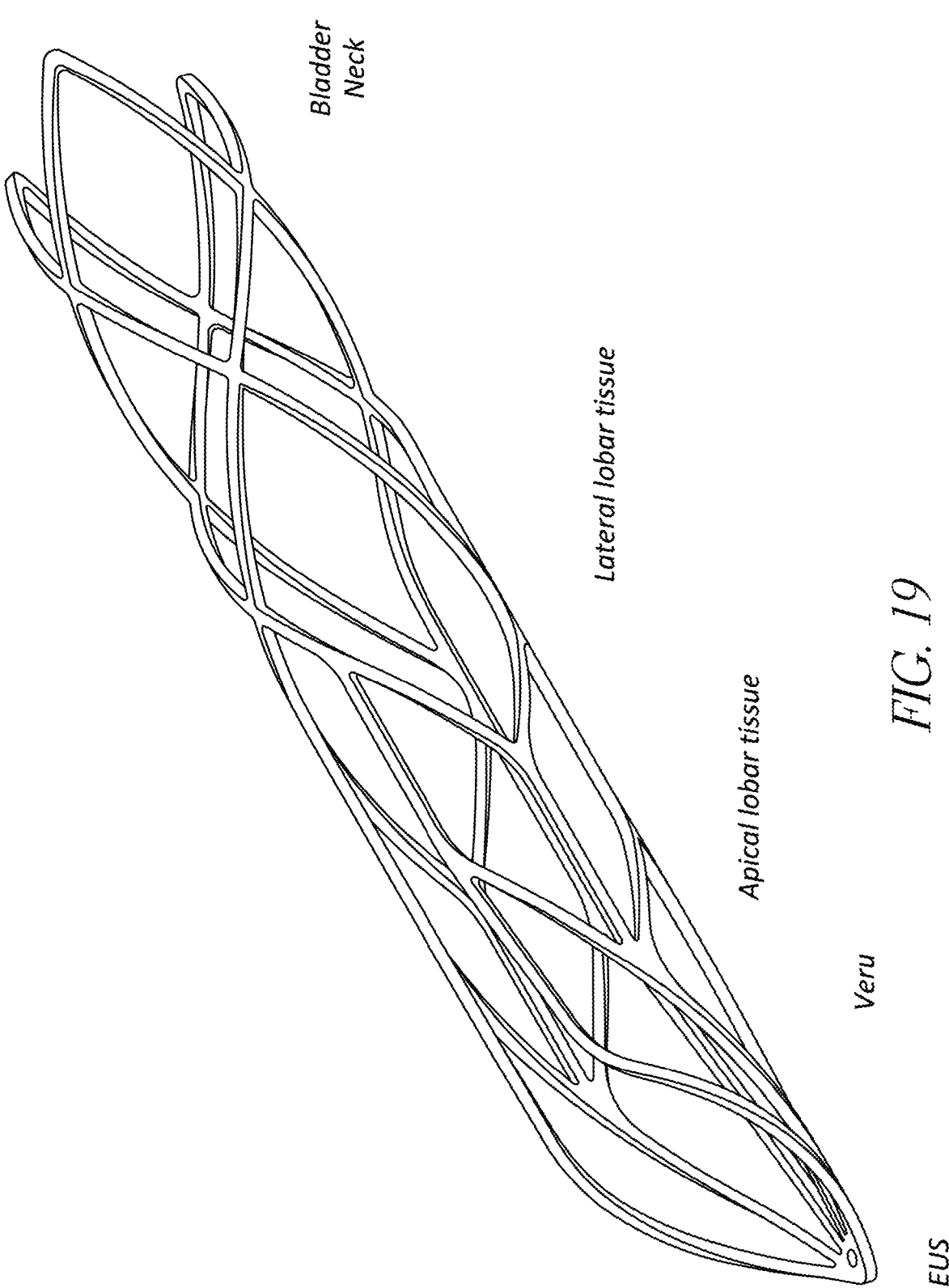
FIGS. 19-22 illustrates another embodiment of a urethral stent configured to be positioned within the prostatic urethra, as shown in FIG. 2.
Figure 20:
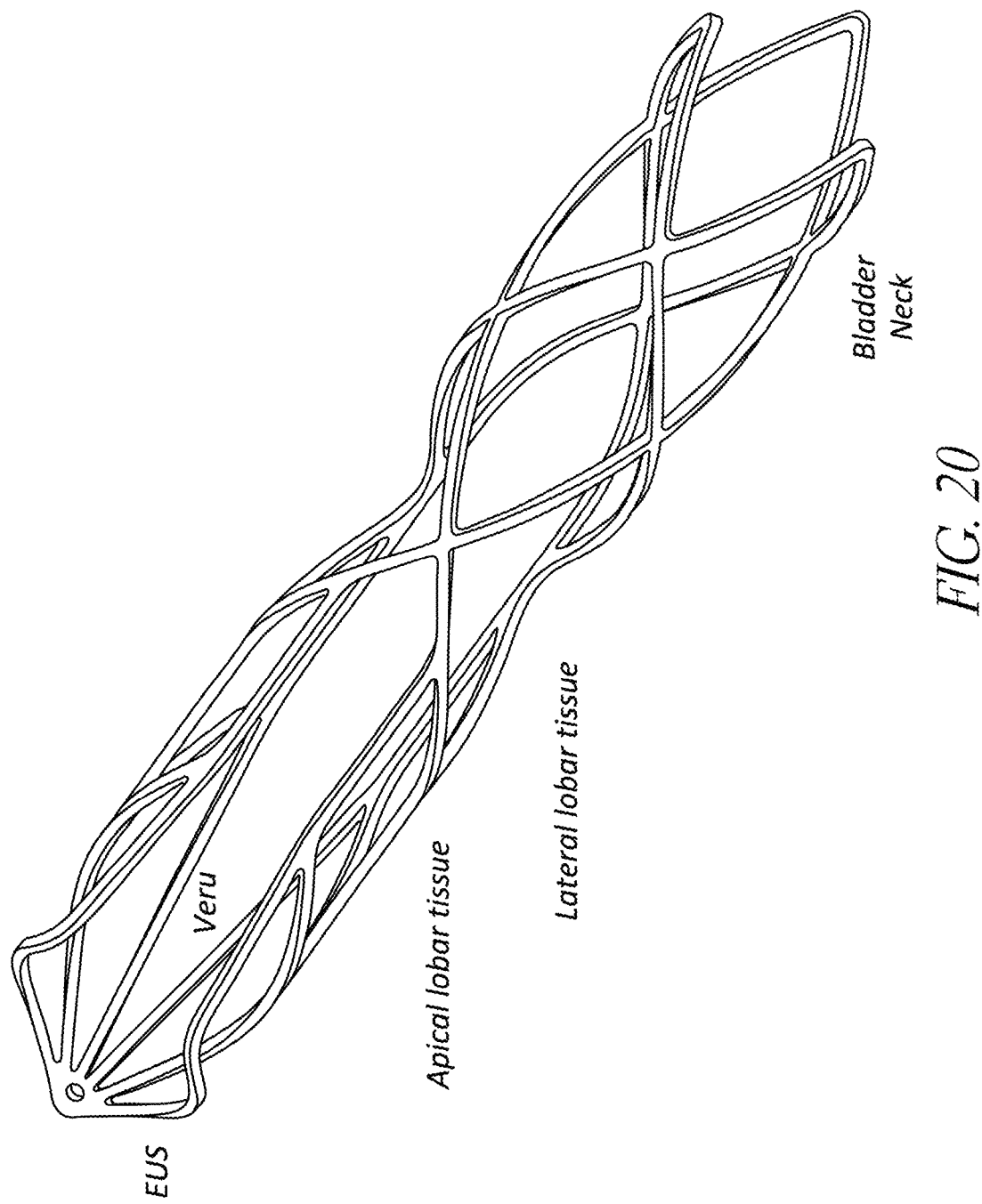
Figure 21:
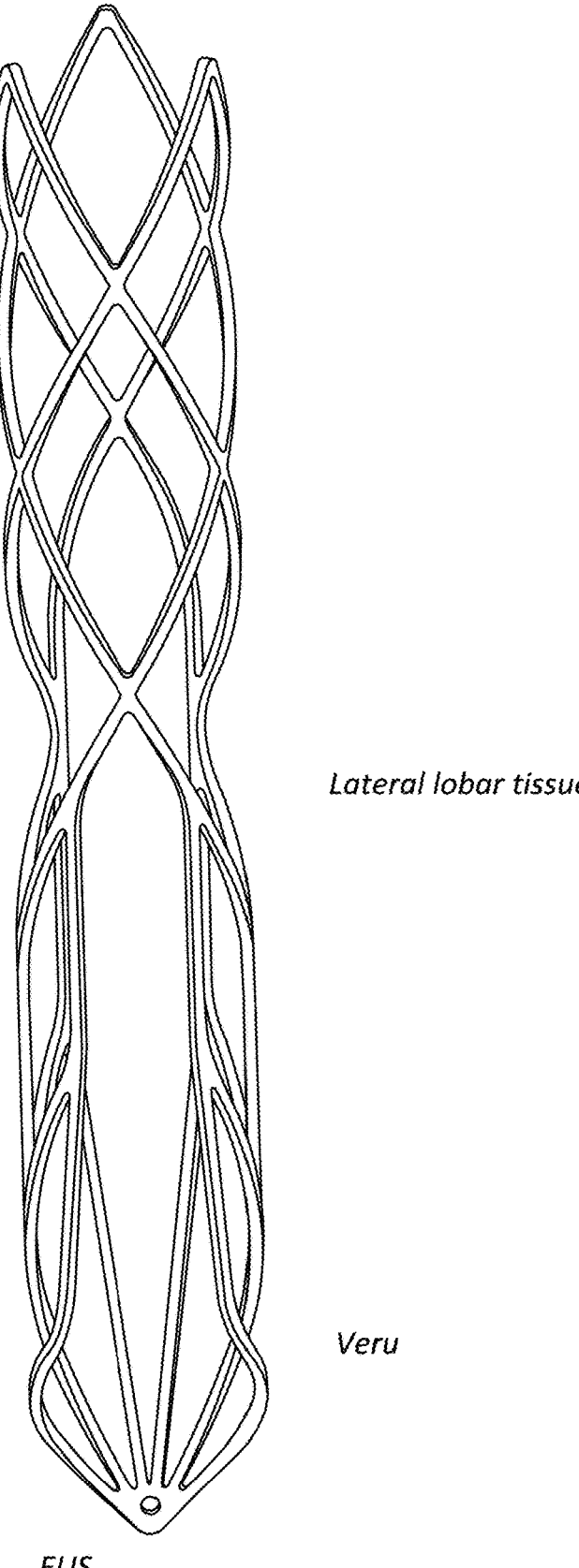
Figure 22:
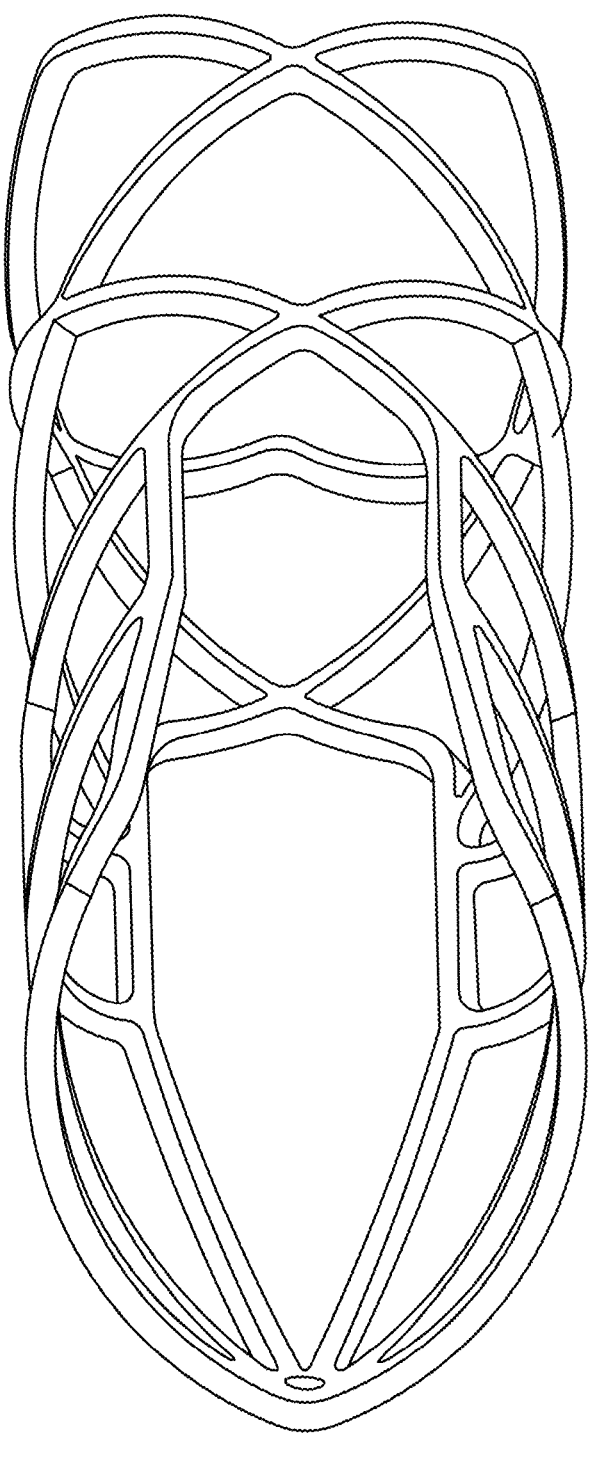

In the embodiment of FIGS. 14-16, the longitudinal struts along one line are about the same length while the longitudinal struts along a circumferentially adjacent line increase in the proximal direction. The stent of FIG. 17 has a cylindrical shape when expanded, and the cells are progressively longer in the proximal direction. The stent of FIG. 18 has a helical tail segment. The stent of FIGS. 19-22 includes an open superior region to further control the radial force provided by the stent with deployed into its expanded configuration.

The stents described herein may be further described by their length, expanded diameter, collapsed diameter, angle values, and strut/wall thickness. A variety of values and combinations of values are possible and should not be limited to the following examples. In some embodiments, the stent has an outside, expanded diameter in the range of about 8 mm to about 12 mm. The overall length of the stent may be in the range of about 25 mm to about 55 mm. The nose segment of the stent may have a length of about 10 mm and the body may have a length of about 15 mm and the length of the tail may be selected such that the overall stent length matches the patient's anatomy. For example, the tail segment may have a length of about 5 mm to about 30 mm. The acute angles within the stent cells may be in the range of 5 to 85 degrees, 10 to 60 degrees or 20 to 50 degrees. The obtuse angles within the stent may be in the range of 95 to 175 degrees, 120 to 170 degrees, or 110 to 150 degrees. The strut and wall thickness of the stent can be in the range of 0.025 mm and 1.0 mm.

Other Considerations

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting the device proximate to the distal end of the prostatic urethra" includes "instructing the inserting a device proximate to the distal end of the prostatic urethra." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A device for maintaining patency of a prostatic urethra, comprising:

a stent comprising a proximal end, a distal end, and a passageway therebetween configured to facilitate flow of body fluids therebetween, the stent further comprising a plurality of longitudinal and angled struts and nodes, each longitudinal strut coupled to at least one angled strut at a corresponding node, the struts and nodes coupled to each other to form a plurality of cells, circumferentially adjacent cells forming stent regions, the stent further comprising a nose region extending from and including the stent distal end, a body region, and a tail region extending from and including the stent proximal end, wherein the body region extends between the nose and tail regions, the stent configured to expand from a compressed configuration to an expanded configuration within a bodily lumen; and a catheter, wherein the stent is mounted on the catheter such that the stent proximal end and tail region are configured to be released first from the catheter when deployed, and such that the stent distal end and nose region are configured to be released last from the catheter when deployed;

wherein the stent further comprises a collapsibility gradient along its length such that it provides a nose region radial force at the nose region, a body region radial force at the body region, and a tail region radial force at the tail region, wherein the nose region radial force is less than the tail region radial force, and the tail region radial force is less than the body region radial force.

2. The device of claim 1, wherein struts in the nose region are connected to form a loop.

3. The device of claim 1, wherein the length of the longitudinal struts in the body region are the same.

4. The device of claim 1, wherein the length of the some colinear longitudinal struts in the tail region are the same length, and the lengths of other colinear longitudinal struts in the tail region are different from one another.

5. The device of claim 1, wherein the lengths of colinear longitudinal struts in the tail region increase from an end of the body region to an end of the tail region.

6. The device of claim 1, wherein the cells form parallelograms.

7. The device of claim 1, wherein the cells form trapezium shapes.

8. The device of claim 1, wherein the cells form irregular quadrilaterals.

9. The device of claim 1, wherein the angled struts are arranged such that pulling the stent into a working channel of a delivery device causes the stent to radially compress into its compressed configuration.

10. The device of claim 1, wherein nodes located at an end of the tail region form atraumatic tips configured to engage soft tissue at the proximal prostatic urethra and to prevent proximal migration of the stent when implanted within the prostatic urethra.

11. The device of claim 1, wherein the tail region is flared when in the expanded configuration.

12. The device of claim 1, wherein the stent is cylindrical when in the expanded configuration.

13. The device of claim 1, wherein acute angles between angled and longitudinal struts decrease in magnitude moving towards the stent's proximal end at an end of the tail region.

14. The device of claim 1, wherein obtuse angles between angled and longitudinal struts increase in magnitude moving towards the stent's proximal end at an end of the tail region.

15. The device of claim 1, wherein the stent is formed from a cylinder of shape memory metal.

16. The device of claim 1, wherein the stent is formed from a cylinder of stainless steel.

17. The device of claim 1, further comprising a coating on at least an outside surface of the stent.

18. A system for maintaining the patency of a prostatic urethra comprising the stent of claim 1 and a delivery device.

19. The system of claim 18, wherein the delivery device comprises a cystoscope.

20. The system of claim 18, further comprising a control member configured to releasably couple to the stent and to fit within a working channel of the delivery device.

21. A method of deploying a stent to maintain the patency of a prostatic urethra, comprising:

providing a device as in claim 1;

coupling the device to a delivery device with a control member;

loading the control member and device into a working channel of the delivery device;

advancing the delivery device to a proximal prostatic urethra;

deploying at least part of the tail region of the stent within a bladder;

withdrawing the stent into the prostatic urethra such that an end of the tail region is at the proximal prostatic urethra;

decoupling the device from the control member and delivery device; and withdrawing the control member and delivery device from the urethra.

22. The method of claim 21, further comprising anchoring the device in the prostatic urethra by embedding atraumatic tips at an end of the tail region in soft tissue at the proximal prostatic urethra and to prevent proximal migration of the stent.

23. The method of claim 21, wherein loading the control member and device into the working channel of the delivery device comprises advancing the control member and the device in a retrograde direction through the working channel.

* * * * *